US009737419B2

(12) United States Patent
Herr et al.

(10) Patent No.: US 9,737,419 B2
(45) Date of Patent: Aug. 22, 2017

(54) BIOMIMETIC TRANSFEMORAL PROSTHESIS

(71) Applicant: BIONX MEDICAL TECHNOLOGIES, INC., Bedford, MA (US)

(72) Inventors: Hugh Miller Herr, Somerville, MA (US); Christopher Williams, Pittsburgh, PA (US); Christopher Eric Barnhart, Carlisle, MA (US); Zhixiu Han, Acton, MA (US); Charles E. Rohrs, Newton, MA (US); Richard J. Casler, Jr., Lowell, MA (US)

(73) Assignee: BIONX MEDICAL TECHNOLOGIES, INC., Bedford, MA (US)

( * ) Notice: Subject to any disclaimer, the term of this patent is extended or adjusted under 35 U.S.C. 154(b) by 0 days.

(21) Appl. No.: 14/355,657

(22) PCT Filed: Nov. 2, 2012

(86) PCT No.: PCT/US2012/063395
§ 371 (c)(1),
(2) Date: May 1, 2014

(87) PCT Pub. No.: WO2013/067407
PCT Pub. Date: May 10, 2013

(65) Prior Publication Data
US 2014/0296997 A1  Oct. 2, 2014

Related U.S. Application Data

(60) Provisional application No. 61/554,921, filed on Nov. 2, 2011.

(51) Int. Cl.
*A61F 2/64* (2006.01)
*A61F 2/66* (2006.01)
(Continued)

(52) U.S. Cl.
CPC .............. *A61F 2/68* (2013.01); *A61F 2/4657* (2013.01); *A61F 2/64* (2013.01); *A61F 2/6607* (2013.01);
(Continued)

(58) Field of Classification Search
None
See application file for complete search history.

(56) References Cited

U.S. PATENT DOCUMENTS

| 45,169 A | 11/1864 | Neubert |
| 360,446 A | 4/1887 | Kreemer |

(Continued)

FOREIGN PATENT DOCUMENTS

| EP | 1 393 866 | 3/2004 |
| EP | 1 408 892 | 4/2004 |
| EP | 1 534 117 | 6/2005 |
| JP | 2005-000500 | 1/2005 |

(Continued)

OTHER PUBLICATIONS

Wikipedia document entitled "Motor Controller", downloaded on Jul. 12, 2016.*

(Continued)

*Primary Examiner* — David H Willse

(57) ABSTRACT

In an artificial limb system having an actuator coupled to a joint for applying a torque characteristic thereto, a control bandwidth of a motor controller for a motor included in the actuator can be increased by augmenting a current feedback loop in the motor controller with a feed forward of estimated back electromotive force (emf) voltage associated with, the motor. Alternatively, the current loop is eliminated and replaced with a voltage loop related to joint torque. The voltage loop may also be augmented with the feed forward of estimated back emf, to improve the robustness of the motor controller.

22 Claims, 13 Drawing Sheets

(51) Int. Cl.
*A61F 2/70* (2006.01)
*A61F 2/68* (2006.01)
*A61F 2/46* (2006.01)
*A61F 5/01* (2006.01)
*A61F 2/54* (2006.01)
*A61F 2/60* (2006.01)
*A61F 2/76* (2006.01)

(52) U.S. Cl.
CPC .......... *A61F 5/0111* (2013.01); *A61F 5/0123* (2013.01); *A61F 2/54* (2013.01); *A61F 2/60* (2013.01); *A61F 2002/4667* (2013.01); *A61F 2002/6818* (2013.01); *A61F 2002/6827* (2013.01); *A61F 2002/701* (2013.01); *A61F 2002/704* (2013.01); *A61F 2002/7625* (2013.01); *A61F 2002/7645* (2013.01); *A61F 2005/0155* (2013.01)

(56) References Cited

U.S. PATENT DOCUMENTS

| | | |
|---|---|---|
| 595,634 A | 12/1897 | King |
| 2,489,291 A | 11/1949 | Henschke et al. |
| 2,529,968 A | 11/1950 | Sartin |
| 3,098,645 A | 7/1963 | Owens |
| 3,207,497 A | 9/1965 | Schoonover |
| 3,546,712 A | 12/1970 | Tarte |
| 3,844,279 A | 10/1974 | Konvalin |
| 3,987,498 A | 10/1976 | Mason |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,697,808 A | 10/1987 | Larson et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,936,295 A | 6/1990 | Crane |
| 4,964,402 A | 10/1990 | Grim et al. |
| 4,989,161 A | 1/1991 | Oaki |
| 5,012,591 A | 5/1991 | Asakawa |
| 5,038,089 A | 8/1991 | Szakaly |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,282,460 A | 2/1994 | Boldt |
| 5,294,873 A | 3/1994 | Seraji |
| 5,311,109 A | 5/1994 | Ozawa |
| RE34,661 E | 7/1994 | Grim |
| 5,327,790 A | 7/1994 | Levin et al. |
| 5,330,417 A | 7/1994 | Petersen et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,888,213 A | 3/1999 | Sears et al. |
| 5,898,948 A | 5/1999 | Kelly et al. |
| 5,910,720 A | 6/1999 | Williamson et al. |
| 5,932,230 A | 8/1999 | DeGrate |
| 5,944,760 A | 8/1999 | Christensen |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,095,991 A | 8/2000 | Krausman et al. |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,500,138 B1 | 12/2002 | Irby et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,532,400 B1 | 3/2003 | Jacobs |
| 6,585,774 B2 | 7/2003 | Dean, Jr. et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,645,252 B2 | 11/2003 | Asai et al. |
| 6,660,042 B1 | 12/2003 | Curcie et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,755,870 B1 | 6/2004 | Biedermann et al. |
| 6,764,520 B2 | 7/2004 | Deffenbaugh et al. |
| 6,802,382 B2 | 10/2004 | Hattori et al. |
| 6,811,571 B1 | 11/2004 | Phillips |
| 6,821,233 B1 | 11/2004 | Colombo et al. |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,942,629 B2 | 9/2005 | Hepburn et al. |
| 6,945,947 B2 | 9/2005 | Ingimundarson et al. |
| 6,966,882 B2 | 11/2005 | Horst |
| 6,969,408 B2 | 11/2005 | Lecomte et al. |
| 6,992,455 B2 | 1/2006 | Kato et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |

(56) References Cited

U.S. PATENT DOCUMENTS

| | | |
|---|---|---|
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,190,141 B1 | 3/2007 | Ashrafiuon et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,278,954 B2 | 10/2007 | Kawai et al. |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,390,309 B2 | 6/2008 | Dariush |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,628,766 B1 | 12/2009 | Kazerooni et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,770,842 B2 | 8/2010 | Benson |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,874,223 B2 | 1/2011 | Sugar et al. |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |

(56) References Cited

U.S. PATENT DOCUMENTS

| | | | |
|---|---|---|---|
| 7,985,265 B2 | 7/2011 | Moser et al. | |
| D643,537 S | 8/2011 | Lee | |
| 7,992,849 B2 | 8/2011 | Sugar et al. | |
| 7,998,221 B2 | 8/2011 | Lecomte et al. | |
| 8,002,724 B2 | 8/2011 | Hu et al. | |
| 8,007,544 B2 | 8/2011 | Jonsson et al. | |
| 8,016,781 B2 | 9/2011 | Ingimundarson et al. | |
| 8,021,317 B2 | 9/2011 | Arnold et al. | |
| 8,025,632 B2 | 9/2011 | Einarsson | |
| 8,025,699 B2 | 9/2011 | Lecomte et al. | |
| 8,026,406 B2 | 9/2011 | Janusson et al. | |
| D646,394 S | 10/2011 | Tweardy et al. | |
| D647,622 S | 10/2011 | Lee et al. | |
| D647,623 S | 10/2011 | Thorgilsdottir et al. | |
| D647,624 S | 10/2011 | Thorgilsdottir et al. | |
| 8,034,120 B2 | 10/2011 | Egilsson et al. | |
| 8,038,636 B2 | 10/2011 | Thorgilsdottir et al. | |
| 8,043,244 B2 | 10/2011 | Einarsson et al. | |
| 8,043,245 B2 | 10/2011 | Campos et al. | |
| 8,048,007 B2 | 11/2011 | Roy | |
| 8,048,013 B2 | 11/2011 | Ingimundarson et al. | |
| 8,048,172 B2 | 11/2011 | Jonsson et al. | |
| 8,052,760 B2 | 11/2011 | Egilsson et al. | |
| 8,057,550 B2 | 11/2011 | Clausen et al. | |
| 8,075,633 B2 | 12/2011 | Herr et al. | |
| 8,142,370 B2 | 3/2012 | Weinberg et al. | |
| 8,181,520 B2 | 5/2012 | Kadota et al. | |
| 8,202,325 B2 | 6/2012 | Albrecht-Laatsch et al. | |
| 8,287,477 B1 | 10/2012 | Herr et al. | |
| 8,419,804 B2 | 4/2013 | Herr et al. | |
| 8,551,184 B1 | 10/2013 | Herr | |
| 2001/0029400 A1 | 10/2001 | Deffenbaugh et al. | |
| 2002/0052663 A1 | 5/2002 | Herr et al. | |
| 2002/0092724 A1 | 7/2002 | Koleda | |
| 2002/0138153 A1 | 9/2002 | Koniuk | |
| 2003/0093021 A1 | 5/2003 | Goffer | |
| 2003/0120183 A1* | 6/2003 | Simmons | 600/595 |
| 2003/0125814 A1 | 7/2003 | Paasivaara et al. | |
| 2003/0139783 A1 | 7/2003 | Kilgore et al. | |
| 2003/0163206 A1 | 8/2003 | Yasui et al. | |
| 2003/0195439 A1 | 10/2003 | Caselnova | |
| 2004/0039454 A1 | 2/2004 | Herr et al. | |
| 2004/0049290 A1 | 3/2004 | Bedard | |
| 2004/0054423 A1 | 3/2004 | Martin | |
| 2004/0064195 A1 | 4/2004 | Herr | |
| 2004/0083528 A1 | 5/2004 | Stewart et al. | |
| 2004/0088025 A1 | 5/2004 | Gesotti | |
| 2004/0172097 A1 | 9/2004 | Brodard et al. | |
| 2004/0181118 A1 | 9/2004 | Kochamba | |
| 2004/0181289 A1 | 9/2004 | Bedard et al. | |
| 2004/0193286 A1 | 9/2004 | Grundei | |
| 2004/0255711 A1 | 12/2004 | Takenaka et al. | |
| 2004/0261561 A1 | 12/2004 | Takenaka et al. | |
| 2005/0007834 A1 | 1/2005 | Hidaka | |
| 2005/0043614 A1 | 2/2005 | Huizenga et al. | |
| 2005/0049652 A1 | 3/2005 | Tong | |
| 2005/0059908 A1 | 3/2005 | Bogert | |
| 2005/0070834 A1 | 3/2005 | Herr et al. | |
| 2005/0085948 A1 | 4/2005 | Herr et al. | |
| 2005/0094343 A1 | 5/2005 | Mintz | |
| 2005/0155444 A1 | 7/2005 | Otaki et al. | |
| 2005/0179417 A1 | 8/2005 | Takenaka et al. | |
| 2005/0197717 A1 | 9/2005 | Ragnarsdottir et al. | |
| 2005/0209707 A1 | 9/2005 | Phillips et al. | |
| 2005/0228515 A1 | 10/2005 | Musallam et al. | |
| 2005/0251079 A1 | 11/2005 | Carvey et al. | |
| 2006/0004299 A1 | 1/2006 | Endo et al. | |
| 2006/0004307 A1 | 1/2006 | Horst | |
| 2006/0055358 A1 | 3/2006 | Ogawa et al. | |
| 2006/0064047 A1 | 3/2006 | Shimada et al. | |
| 2006/0069448 A1 | 3/2006 | Yasui | |
| 2006/0094989 A1 | 5/2006 | Scott et al. | |
| 2006/0135883 A1 | 6/2006 | Jonsson et al. | |
| 2006/0173552 A1 | 8/2006 | Roy | |
| 2006/0184280 A1 | 8/2006 | Oddsson et al. | |
| 2006/0211956 A1 | 9/2006 | Sankai | |
| 2006/0213305 A1 | 9/2006 | Sugar et al. | |
| 2006/0214621 A1 | 9/2006 | Ogawa et al. | |
| 2006/0214622 A1* | 9/2006 | Summer et al. | 318/568.12 |
| 2006/0224246 A1 | 10/2006 | Clausen et al. | |
| 2006/0249315 A1 | 11/2006 | Herr et al. | |
| 2006/0258967 A1 | 11/2006 | Fujil et al. | |
| 2006/0264790 A1 | 11/2006 | Kruijsen et al. | |
| 2006/0276728 A1 | 12/2006 | Ashihara et al. | |
| 2007/0016329 A1 | 1/2007 | Herr et al. | |
| 2007/0043449 A1 | 2/2007 | Herr et al. | |
| 2007/0050044 A1 | 3/2007 | Haynes et al. | |
| 2007/0050047 A1 | 3/2007 | Ragnarsdottlr et al. | |
| 2007/0123997 A1 | 5/2007 | Herr et al. | |
| 2007/0129653 A1 | 6/2007 | Sugar et al. | |
| 2007/0145930 A1 | 6/2007 | Zaier | |
| 2007/0156252 A1 | 7/2007 | Jonsson et al. | |
| 2007/0162152 A1 | 7/2007 | Herr et al. | |
| 2007/0233279 A1 | 10/2007 | Kazerooni et al. | |
| 2007/0267791 A1 | 11/2007 | Hollander et al. | |
| 2008/0039756 A1 | 2/2008 | Thorsteinsson et al. | |
| 2008/0114272 A1 | 5/2008 | Herr et al. | |
| 2008/0155444 A1 | 6/2008 | Pannese et al. | |
| 2008/0161937 A1 | 7/2008 | Sankai | |
| 2008/0234608 A1 | 9/2008 | Sankai | |
| 2009/0030530 A1 | 1/2009 | Martin | |
| 2009/0171469 A1 | 7/2009 | Thorsteinsson et al. | |
| 2009/0192619 A1 | 7/2009 | Martin et al. | |
| 2009/0222105 A1 | 9/2009 | Clausen | |
| 2010/0004860 A1 | 1/2010 | Chernoguz et al. | |
| 2010/0025409 A1 | 2/2010 | Hunter | |
| 2010/0094188 A1 | 4/2010 | Goffer et al. | |
| 2010/0113980 A1 | 5/2010 | Herr et al. | |
| 2010/0114329 A1 | 5/2010 | Casler et al. | |
| 2010/0174384 A1 | 7/2010 | Herr et al. | |
| 2010/0174385 A1 | 7/2010 | Casler et al. | |
| 2010/0179668 A1 | 7/2010 | Herr et al. | |
| 2010/0312363 A1 | 12/2010 | Herr et al. | |
| 2011/0082566 A1 | 4/2011 | Herr et al. | |
| 2011/0098828 A1 | 4/2011 | Balboni et al. | |
| 2011/0105966 A1 | 5/2011 | Kazerooni et al. | |
| 2011/0224804 A1 | 9/2011 | Clausen et al. | |
| 2011/0245931 A1 | 10/2011 | Clausen et al. | |
| 2011/0257764 A1 | 10/2011 | Herr et al. | |
| 2011/0260380 A1 | 10/2011 | Hollander et al. | |
| 2011/0264230 A1 | 10/2011 | Herr et al. | |
| 2011/0278857 A1 | 11/2011 | Sugar et al. | |
| 2011/0295384 A1 | 12/2011 | Herr et al. | |
| 2011/0295385 A1 | 12/2011 | Herr et al. | |
| 2012/0209405 A1 | 8/2012 | Herr et al. | |
| 2012/0259429 A1 | 10/2012 | Han et al. | |
| 2012/0259430 A1 | 10/2012 | Han et al. | |
| 2012/0259431 A1 | 10/2012 | Han et al. | |
| 2012/0271433 A1 | 10/2012 | Galea et al. | |
| 2012/0283845 A1 | 11/2012 | Herr et al. | |
| 2013/0312483 A1 | 11/2013 | Herr et al. | |
| 2014/0088727 A1 | 3/2014 | Han et al. | |

FOREIGN PATENT DOCUMENTS

| | | |
|---|---|---|
| WO | WO 94/09727 A2 | 5/1994 |
| WO | WO 03/003953 A1 | 1/2003 |
| WO | WO 03/068453 | 8/2003 |
| WO | WO 2004/017872 | 3/2004 |
| WO | WO 2004/019832 | 3/2004 |
| WO | WO 2006/110895 | 10/2006 |
| WO | WO 2007/025116 A2 | 3/2007 |
| WO | WO 2009/011682 A1 | 1/2009 |
| WO | WO 2009/082249 | 7/2009 |
| WO | WO 2010/025403 A1 | 3/2010 |
| WO | WO 2010/025409 | 3/2010 |
| WO | WO 2010/027968 | 3/2010 |
| WO | WO 2011/005482 A2 | 1/2011 |

OTHER PUBLICATIONS

International Search Report and Written Opinion for PCT/US2012/063395 mailed Mar. 1, 2013.

(56) References Cited

OTHER PUBLICATIONS

Abbas J. and Chizeck H., Neural Network Control of Functional Neuromuscular Stimulation Systems: Computer Simulation Studies, IEEE Transactions on Biomedical Engineering, vol. 42, No. 1, Nov. 1995, pp. 1117-1127.

Abul-haj, C. and Hogan, N., Functional assessment of control systems for cybernetic elbow prostheses. Part I, Part II, IEEE Transactions on Biomedical Engineering, vol. 37, No. 11, Nov. 1990, Cambridge, MA, pp. 1037-1047.

Akazawa, K., et. al, Biomimetic EMG prosthesis-hand, Proceedings of the 18th Annual International Conference of the IEEE Engineering in Medicine and Biology Society, vol. 2, Oct. 1996, Amsterdam, Netherlands, pp. 535-536.

Aminian, Estimation of Speed and Incline of Walking Using Neural Network, IEEE Transactions on Biomedical Engineering, vol. 44, No. 3, Jun. 1995, pp. 743-746.

Anderson, F. and Pandy M., Dynamic optimization of human walking, Journal of Biomechanical Engineering, vol. 123, Oct. 2001, pp. 381-390.

Andrews, et al., Hybrid FES Orthosis incorporating closed loop control and sensory feedback, J. Biomed Eng., vol. 10, Apr. 1988, pp. 189-195.

Arakawa et al., Natural motion generation of biped locomotion robot using hierarchical trajectory generation method consisting of GA, EP layers, Proceedings of the 1997 IEEE International Conference on Robotics and Automation, Apr. 1997, Albuquerque, NM, pp. 211-216.

Au et al., Initial experimental study on dynamic interaction between an amputee and a powered ankle-foot prosthesis, Workshop on Dynamic Walking: Mechanics and Control of Human and Robot Locomotion, May 2006, Ann Arbor, MI, p. 1.

Au, S., An EMG-position controlled system for an active ankle-foot prosthesis: an initial experimental study, Proc. of the 2006 IEEE International Conference on Rehabilitation Robotics, Jul. 2005, Chicago, IL, pp. 375-379.

Au, S., et al. An ankle-foot emulation system for the study of human walking biomechanics, Proc. of the 2006 IEEE Int. Conf. on Robotics and Automation, May 2006, Orlando, FL, pp. 2939-2945.

Au, S., et. al., Biomechanical design of a powered ankle-foot prosthesis, Proc. of the 2007 IEEE Int. Conf. on Rehabilitation Robotics, Jun. 2007, Noordwijk, Netherlands, pp. 298-303.

Au, S., et. al., Powered Ankle-foot Prosthesis Improves Walking Metabolic Economy, IEEE Trans. on Robotics, vol. 25, No. 1, Feb. 2009, pp. 51-66.

Au, S., et. al., Powered ankle-foot prosthesis to assist level-ground and stair-descent gaits, Neural Networks, vol. 21, No. 4, Mar. 2008, pp. 654-666.

Au., et. al., Powered Ankle-Foot Prosthesis for the Improvement of Amputee Ambulation, Proceedings of the 29th Annual International Conference of the IEEE, Aug. 2007, Lyon, France, pp. 3020-3026.

Barth, D.., et. al., Gait analysis and energy cost of below-knee amputees wearing six different prosthetic feet, Journal of Prosthetics & Orthotics, vol. 4, No. 2, Winter, 1992, pp. 63-75.

Baten, et al., Inertial Sensing in Ambulatory back load Estimation, 18 Annual International Conferences of IEEE Engineering in Medicine and Biology Society, Amsterdam 1996, pp. 497-498.

Bateni, H. and Olney S., Kinematic and kinetic variations of below-knee amputee gait, Journal of Prosthetics & Orthotics, vol. 14, No. 1, Mar. 2002, pp. 2-13.

Blaya et al., Adaptive control of a variable-impedance ankle-foot orthosis to assist drop-foot gait, IEEE Transactions on Neural Systems and Rehabilitation Engineering, vol. 12, No. 1, Mar. 2004, pp. 24-31.

Blaya, et al., Active Ankle Foot Orthoses (AAFO). http://www.ai.mit.edu. Artificial Intelligence Laboratory, Massachusetts Institute of Technology, Cambridge, Massachusetts. 2001. 251-253.

Blickhan, R., The spring-mass model for running and hopping, J of Biomech. Feb. 22, 1989, Great Britain, pp. 1217-1227.

Bortz, A New Mathematical Formulation for Strapdown Inertial Navigation, IEEE Transactions of Aerospace and Electronic Systems, vol. AES-7, No. 1, Jan. 1971, p. 61-66.

Bouten et al., Assessment of energy expenditure for physical activity using a triaxial accelerometer. Med Sci Sports Exerc. Dec. 1994;26(12):1516-23.

Bouten, A Triaxial Accelerometer and Portable Data Processing Unit for the Assessment of Daily Physical Activity, IEEE Transactions on Biomedical Engineering, vol. 44, No. 3, Mar. 1997, pp. 136-147.

Brockway, J., Derivation of formulae used to calculate energy expenditure in man, Human Nutrition Clinical Nutrition, vol. 41, Nov. 1987, pp. 463-471.

Brown, R., On the nature of the fundamental activity of the nervous centres: together with an analysis of the conditioning of rhythmic activity in progression, and a theory of the evolution of function in the nervous system, J Physiol, vol. 48,No. 1, Mar. 1914, pp. 18-46.

Chang, et al., Ischemic Colitis and Complications of Constipation Associated with the use of Alosetron Under a Risk Management Plan: Clinical Characteristics, Outcomes, and Incidences The Americal Journal of Gastronenterology, vol. 105, No. 4, Apr. 2010, pp. 866-875.

Chu, A., Kazerooni, H. and Zoss, A., On the Biomimetic Design of the Berkeley Lower Extremity Exoskeleton (BLEEX), Proceedings of the 2005 IEEE International Conference on Robotics and Automation, Apr. 2005, Barcelona, Spain, pp. 4356-4363.

Colborne, G. R., S. Naumann, P. E. Longmuir, and D. Berbrayer, Analysis of mechanical and metabolic factors in the gait of congenital below knee amputees, Am. J. Phys. Med. Rehabil., vol. 92, pp. 272-278, Oct. 1992.

Colgate, The control of dynamically interacting systems. MIT. Aug. 1988. 1-19.

Collins, et al., Controlled Energy Storage and Return Prosthesis Reduces Metabolic cost of Walking, ASB 29.sup.th Annual Meeting, Cleveland, Ohio, Jul. 31-Aug. 5, 2005, 1 page.

Collins, et al., Supporting Online Material for Efficient bipedal robots based on passive-dynamic walkers, Mechanical Engineering, University of Michigan, Feb. 2005, Ann Arbor, MI, pp. 1-8.

Crago P., et. al., New Control Strategies for neuroprosthetic systems, Journal of Rehabilitation Research and Development, vol. 33, No. 2, Apr. 1996, pp. 158-172.

Daley, M. A., Felix, G., Biewener, A. A., 2007. Running stability is enhanced by a proximo-distal gradient in joint neuromechanical control. J Exp Biol 210 (Pt 3), Nov. 2006, pp. 383-394.

Dapena, J. and McDonald, C., Three-dimensional analysis of angular momentum in the hammer throw, Med. Sci. in Sports Exerc., vol. 21, No. 2, Apr. 1989, pp. 206-220.

Davids et al., Disorders of Bone and Mineral Metabolism. Book reviews. J Ped Orthopaedics. 1992;12(6):815.

Dietz, V., Proprioception and locomotor disorders, Nat Rev Neurosci, vol. 3, Oct. 2002, pp. 781-790.

Dietz, V., Spinal Cord Pattern Generators for Locomotion, download Feb. 6, 2012, http://www.Clinph-journal.com/article/PIIS1388245703001202/fullt- ext, 12 pages.

Doerschuk, et. al., Upper extremity limb function discrimination using EMG signal analysis, IEEE Transactions on Biomedical Engineering. vol. 30., No. 1., Jan. 1983, pp. 18-28.

Doke, J., et. al., Mechanics and energetics of swinging the human leg, The Journal of Experimental Biology, vol. 208, Feb. 2005, pp. 439-445.

Donelan, J., et. al. Simultaneous positive and negative external mechanical work in human walking, Journal of Biomechanics, vol. 35, Jan. 2002, pp. 117-124.

Donelan, J., et. al., Force regulation of ankle extensor muscle activity in freely walking cats, J Neurophysiol, vol. 101, No. 1, Nov. 2008, pp. 360-371.

Donelan, J., et. al., Mechanical work for step-to-step transitions is a major determinant of the metabolic cost of human walking, J. Exp. Biol., vol. 205, Dec. 2002, pp. 3717-3727.

Drake, C., Ankle & Foot Splints or Orthoses (AFOs), HemiHelp, Last updated Jun. 2009, 8 pages.

Drake, Foot & Ankle Splints or Orthoses. HemiHelp Information Sheet, London, United Kingdom. Jun. 2009;1-5.

(56) References Cited

OTHER PUBLICATIONS

Eilenberg, M., A Neuromuscular-Model Based Control Strategy for Powered Ankle-Foot Prostheses, Masters Thesis, Massachusetts Institute of Technology, Cambridge, Mass., 2009.

Ekeberg, O. and Grillner, S., Simulations of neuromuscular control in lamprey swimming, Philos Trans R Soc Lond B Biol Sci, vol. 354, May 1999, pp. 895-902.

Ekeberg, O. and Pearson, K., Computer simulation of stepping in the hind legs of the cat: an examination of mechanisms regulating the stance-to-swing transition, J Neurophysiol, vol. 94, No. 6, Jul. 2005, pp. 4256-4268.

Endo, K., et. al., A quasi-passive model of human leg function in level-ground walking, Proc. of 2006 IEEE/RSJ International Conference on Intelligent Robots and Systems (IROS), Oct. 2006, Beijing, China, pp. 4935-4939.

Eppinger, S. Seering W., Three dynamic problems in robot force control, IEEE Transactions on Robotics and Automation, vol. 8, No. 6, Dec. 1992, pp. 751-758.

Esquenazi, A. and DiGiacomo, R., Rehabilitation After Amputation, Journ Am Podiatr Med Assoc, vol. 91, No. 1, Jan. 2001, pp. 13-22.

Farley, C. and McMahon, T., Energetics of walking and running: insights from simulated reduced-gravity experiments, The American Physiological Society, Dec. 1992, pp. 2709-2712.

Farry, K. A., et al., Myoelectric teleoperation of a complex robotic hand, IEEE Transactions on Robotics and Automation. vol. 12, No. 5, Oct. 1996, pp. 775-788.

Featherstone, R., 1987, Robot Dynamic Algorithms, Boston, Mass., Kluwer Academic Publishers, pp. 155-172.

Fisekovic et al., New controller for functional electrical stimulation systems, Medical Engineering & Physics vol. 23, 2001, pp. 391-399.

Fite, K., et. al., Design and Control of an Electrically Powered Knee Prosthesis, Proc. of 2007 IEEE 10th International Conference on Rehabilitation Robotics (ICORR), Jun. 2007, pp. 902-905.

Flowers, W. A Man-Interactive Simulator System for Above-Knee Prosthetic Studies, Ph.D. thesis, Massachusetts of Institute Technology, Department of Mechanical Engineering. Jul. 10, 1973.

Fod, A., et. al., Automated Derivation of Primitives for Movements Classification, Autonomous Robots, vol. 12, No. 1, Jan. 2002, pp. 39-54.

Foerster et al., Detection of posture and motion by accelerometry a validation study in ambulatory monitoring, Computer in Human Behavior, 1999, pp. 571-583.

Foxlin et al., Miniature 6-DOF inertial system for tracking HMDs, In SPIE vol. 3362, Helmet and Head-Mounted Displays III, AeroSense 98, Orlando, FL, Apr. 13-14, 1998, 15 pages.

Frigon, A. and Rossignol, S., Experiments and models of sensorimotor interactions during locomotion, Biol Cybern, vol. 95, No. 6, Nov. 2006, pp. 607-627.

Fujita K, et. al., Joint angle control with command filter for human ankle movement using functional electrical stimulation, Proc. of IEEE Ninth Annual Conference for the Engineering in Medicine and Biology Society, Nov. 1987, Boston, MA, pp. 1719-1720.

Fukuda, O. et al., A human-assisting manipulator teleoperated by EMG signals and arm motions, IEEE Transactions on Robotics and Automation. vol. 19, No. 2, Apr. 2003, pp. 210-222.

Gates, D., Characterizing ankle function during stair ascent, descent, and level walking for ankle prosthesis and orthosis design, Masters thesis, Boston University, 2004, pp. 1-82.

Gerritsen et. al., Direct dynamics simulation of the impact phase in heel-toe running, J. Biomech., vol. 28, No. 6, Jun. 1995, Great Britain, pp. 661-668.

Geyer, H. and Herr H., A muscle-reflex model that encodes principles of legged mechanics predicts human walking dynamics and muscle activities, IEEE Transactions on Neural Systems and Rehabilitations Engineering, vol. 18, No. 3, Jun. 2010, pp. 263-273.

Geyer, H., et. al., Compliant leg behaviour explains the basic dynamics of walking and running, Proc. R. Soc. Cond. B 273, Aug. 2006, pp. 2861-2867.

Geyer, H., et. al., Positive force feedback in bouncing gaits?, Proceedings of Royal Society B—Biological Sciences, vol. 270, No. 1529, Aug. 2003, pp. 2173-2183, 2003.

Ghigliazza, R., et. al., A simply stabilized running model, SIAM J. Applied. Dynamical Systems, vol. 2, No. 2, May 2004, pp. 187-218.

Giszter et al., Convergent force fields organized in the frog's spinal cord. J Neurosci. Feb. 1993;13(2):467-91.

Godha, el al., Integrated GPS/INS System for Pedestrian Navigation in a Signal Degraded Environment, ION GNSS, Sep. 2006, Fort Worth, TX, pp. 1-14.

Goswami, A. and Kallem, V., Rate of change of angular momentum and balance maintenance of biped robots, Proceedings of the 2004 IEEE International Conference on Robotics and Automation, Apr. 2004, New Orleans, La., pp. 3785-3790.

Goswami, A., Postural stability of biped robots and the foot-rotation indicator (FRI) point, International Journal of Robotics Research, vol. 18, No. 6, Jun. 1999, pp. 523-533.

Graupe, D., et al., A microprocessor system for multifunctional control of upper-limb prostheses via myoelectric signal identification, IEEE Transaction on Automatic Control. vol. AC-23, vol. 4, Aug. 1978, pp. 538-544.

Gregoire, L., and et al, Role of mono- and bi-articular muscles in explosive movements, International Journal of Sports Medicine 5, 614-630. Dec. 1984. 301-305.

Grillner, S. and Zangger, P., On the central generation of locomotion in the low spinal cat, Exp Brain Res, vol. 34, No. 2, Jan. 1979, pp. 241-261.

Grimes, D. L., An active multi-mode above-knee prosthesis controller, Ph.D. Thesis, Massachusetts Institute of Technology, Jul. 20, 1979.

Gu, W., The Regulation of Angular Momentum During Human Walking, Undergraduate Thesis, Massachusetts Institute of Technology, Physics Department, Jun. 2003, pp. 2-48.

Gunther, M. and Ruder, H., Synthesis of two-dimensional human walking: a test of the A-model, Biol. Cybern., vol. 89, May 2003, pp. 89-106.

Gunther, M., et. al., Human leg design: optimal axial alignment under constraints, J. Math. Biol., vol. 48, Mar. 2004, pp. 623-646.

Hanafusa et al., A Robot Hand with Elastic Fingers and Its Application to Assembly Process, pp. 337-359, Robot Motion, Brady et al., MITPress, Cambridge, MA, 1982.

Hansen, A. H., Childress, D. S., Miff, S. C., Gard, S. A., Mesplay, K. P., The human ankle during walking: implication for the design of biomimetic ankle prosthesis, Journal of Biomechanics, vol. 37, No. 10, Oct. 2004, pp. 1467-1474.

Hashimoto et al., An instrumented compliant wrist using a parallel mechanism, Japan/USA Symposim on Flexible Automation, vol. 1, pp. 741-744, ASME, 1992.

Hayes et al., Leg Motion Analysis During Gait by Multiaxial Accelerometry: Theoretical Foundations and Preliminary Validations, Journal of Biomechanical Engineering, vol. 105, Aug. 1983, pp. 283-289.

Heglund, A Simple Design for a Force-Plat to Measure Ground Reaction Forces, J. exp. Biol., vol. 93, pp. 333-338, 1981.

Herr, H. and Wilkenfeld A., User-adaptive control of a magnetorheological prosthetic knee, Industrial Robot: An International Journal, vol. 30, No. 1, 2003, pp. 42-55.

Herr, H., et. al, A model of scale effects in mammalian quadrupedal running, J Exp Biol 205 (Pt 7), Apr. 2002, pp. 959-967.

Herr, New Horizons for Orthotic and Prosthetic Technology: Artificial Muscle for Ambulation. MIT Media Laboratory. 2004:1-9.

Heyn et al., The Kinematice of the Swing Phase Obtained from Accelerometer and Gyroscope Measurements, 18.sup.th Annual International Conference of the IEEE Engineering in Medicine and Biology Society, Nov. 1996, Amsterdam, Netherlands, pp. 463-464.

Hill, V., The heat of shortening and the dynamic constants of muscle, Proceedings of the Royal Society London B, vol. 126, No. 843, Oct. 1938, pp. 136-195.

Hirai, K., et al., The development of Honda humanoid robot, Proceedings on IEEE/RSJ International Conference on Intelligent Robots and Systems, May 1998, Leuven, Belgium, pp. 1321-1326.

Hitt, J., R. Bellman, M. Holgate, T. Sugar, and K. Hollander, The sparky (spring ankle with regenerative kinetics) projects: Design

(56) References Cited

OTHER PUBLICATIONS and analysis of a robotic transtibial prosthesis with regenerative kinetics, in Proc. IEEE Int. Conf. Robot. Autom.Orlando, Fla., pp. 1587-1596, Sep. 2007.
Hof. A., et. al., Calf muscle moment, work and efficiency in level walking; role of series elasticity, Journal of Biomechanics, vol. 16, No. 7, Sep. 1983, pp. 523-537.
Hofbaur, M. and Williams, B., Hybrid Diagnosis with Unknown Behavioral Modes, Proceedings of the 13.sup.th International Workshop on Principles of Diagnosis (DX02), May 2002, pp. 1-10.
Hofbaur, M. and Williams, B., Mode Estimation of Probabilistic Hybrid Systems, HSSC 2002, LNCS 2289, Mar. 25, 2002, pp. 253-266.
Hofmann, A., et. al., A Sliding Controller for Bipedal Balancing Using Integrated Movement of Contact and Non-Contact Limbs, Proceedings of the IEEE/RSJ International Conference on Intelligent Robots and Systems, Sep. 2004, Sendai, Japan, pp. 1952-1959.
Hofmann, A., et. al., Robust Execution of Bipedal Walking Tasks from Biomechanical Principles, Doctor of Philosophy at the Massachusetts Institute of Technology, Jan. 2006, 407 pages.
Hogan, N and Buerger S., Impedance and Interaction Control, Robotics and Automation Handbook, CRC Press, Jun. 2004, pp. 19.1-19.24.
Hogan, N. (1976) A review of the methods of processing EMG for use as a proportional control signal. Biomedical Engineering. pp. 81-86.
Hogan, N., Impedance Control: An Approach to Manipulation: Part I—Theory, Journal of Dynamic Systems, Measurement , and Control, vol. 107, Mar. 1985, pp. 1-7.
Hollander, K. W., T. G. Sugar, and D. E. Herring, Adjustable robotic tendon using a 'Jack Springs'.TM., Proceedings on IEEE International Conference on Rehabilitation Robotics, Chicago, pp. 113-118, Jun. 28, 2005.
Howard, Joint and Actuator Design for Enhanced Stability in Robotic Force Control, Ph.D. thesis, Massachusetts Inst. of Technology, Dept. of Aeronautics and Astronautics, Sep. 19, 1990.
Huang, H. and Chen. C., Development of a myoelectric discrimination system for a multi-degree prosthetic hand, Proceeding of the 1999 IEEE International Conference on Robotics and Automation, May 1999, Detroit, MI, pp. 2392-2397.
Huang, Q., Planning walking patterns for a biped robot, IEEE Transactions on Robotics and Automation, vol. 17, No. 3, Jun. 2001, pp. 280-289.
Hultborn, H., Spinal reflexes, mechanisms and concepts: from Eccles to Lundberg and beyond, Prog Neurobiol, vol. 78, Feb. 2006, pp. 215-232.
Ijspeert, A. J., 2008, Central pattern generators for locomotion control in animals and robots: a review, Neural Netw, vol. 21, No. 4, May 2008, pp. 642-653.
Ijspeert, A., et. al., From swimming to walking with a salamander robot driven by a spinal cord model, Science, vol. 315, No. 5817, Mar. 2007, pp. 1416-1420.
Isakower, Design Charts for Torsional Properties of Non-circular Shafts, Technical Report ARMIDTR-78001, ARRADCOM, MISD, DRDAR-MSA, Dover,NJ, Nov. 1978.
Ivashko, D., et. al, Modeling the spinal cord neural circuitry controlling cat hindlimb movement during locomotion, Neurocomputing, vol. 52-54, Mar. 2003, pp. 621-629.
Johansson, J., et al., A clinical comparison of variable damping and mechanically passive prosthetic knee devices, American Journal of Physical Medicine & Rehabilitation, vol. 84, No. 8, Aug. 2005, pp. 563-575.
Johnson, C. and Lorenz R., Experimental identification of friction and its compensation in precise, position controlled mechanisms, IEEE Trans. on Industry Applications, vol. 28, No. 6, Dec. 1992, pp. 1392-1398.
Jonic S, et. al., Three machine learning techniques for automatic determination of rules to control locomotion, IEEE Trans Biomed Eng, vol. 46, No. 3, Mar. 1999, pp. 300-310.
Kadaba, M., et. al., Measurement of lower extremity kinematics during level walking, J. Orthop. Res., vol. 8, May 1990, pp. 383-392.
Kadaba, M., et. al., Repeatability of kinematic, kinetic, and electromyographic data in normal adult gait, J. Orthop. Res., vol. 7, Nov. 1989, pp. 849-860.
Kajita, K., et. al., Biped walking on a low friction floor, Proceedings of the 2004 IEEE/RSJ International Conference on Intelligent Robots and Systems, Oct. 2004, Sendai, Japan., pp. 3546-3551.
Kajita, S., et. al., A Hop towards Running Humanoid Biped, Proceedings of the 2004 IEEE International Conference on Robotics and Automation, Apr. 2004, New Orleans, La., pp. 629-635.
Kajita, S., et. al., Resolved Momentum Control: Humanoid Motion Planning based on the Linear and Angular Momentum, Proceedings of the 2003 IEEE/RSJ International Conference on Intelligent Robots and Systems, Oct. 2003, Las Vegas, Nev., pp. 1644-1650.
Kaneko, K., et al., Humanoid robot HRP-2, Proc. IEEE Int. Conf. on Robotics and Automation, Apr. 2004, New Orleans, La., pp. 1083-1090.
Kapti, A. and Yucenur M., Design and control of an active artificial knee joint, Mechanism and Machine Theory, vol. 41, Apr. 2006, pp. 1477-1485.
Katic, D. and Vukobratovic, M., Survey of intelligent control techniques for humanoid robots, Journal of Intelligent and Robotics Systems, vol. 37, Jun. 2003, pp. 117-141.
Kerrigan, D, et. al., A refined view of thedeterminants of gait: significance of heel rise, Arch. Phys. Med. Rehab., vol. 81, Aug. 2000, pp. 1077-1080.
Kerrigan, D, et. al., Quantification of pelvic rotation as a determinant of gait, Arch. Phys. Med. Rehab., vol. 82, Feb. 2001, pp. 217-220.
Khatib, O., et. al., Coordination and decentralized cooperation of multiple mobile manipulators, Journal of Robotic Systems, vol. 13, No. 11, Nov. 1996, pp. 755-764.
Khatib, O., et. al., Whole body dynamic behavior and control of human-like robots, International Journal of Humanoid Robotics, vol. 1, No. 1, Mar. 2004, pp. 29-43.
Kidder, et al., A System for the Analysis of Foot and Ankle Kinematics During Gait, IEEE Transactions on Rehabilitation Engineering, vol. 4, No. 1, Mar. 1996, pp. 25-32.
Kirkwood C, et. al., Automatic detection of gait events: a case study using inductive learning techniques., J Biomed Eng, vol. 11, Nov. 1989, pp. 511-516.
Kitayama, I., Nakagawa N, Amemori K, A microcomputer controlled intelligent A/K prosthesis, Proceedings of the 7th' World Congress of the International Society for Prosthetics and Orthotics, Chicago. Jun. 28, 1992.
Klute et al.,Variable Stiffness Prosthesis for Transtibial Amputees. Dept of Veteran Affairs, Seattle, WA USA, 2005. 2 pages.
Klute, G., et. al., Mechanical properties of prosthetic limbs adapting to the patient, Journal of Rehabilitation Research and Development, vol. 38, No. 3, May 2001, pp. 299-307.
Koganezawa, K. and Kato, I., Control aspects of artificial leg, IFAC Control Aspects of Biomedical Engineering, 1987, pp. 71-85.
Kondak, K. and Hommel, G., Control and online computation of stable movement for biped robots, Proc. of the 2003 IEEE/RSJ International Conference on Intelligent Robots and Systems (IROS), Oct. 2003, Las Vegas, Nev., pp. 874-879.
Kostov A., et. al., Machine learning in control of functional electrical stimulation (FES) systems for locomotion, IEEE Trans on Biomed Eng, vol. 42, No. 6, Jun. 1995, pp. 541-551.
Kuo, A., A simple model of bipedal walking predicts the preferred speed-step length relationship, Journal of Biomechanical Engineering, vol. 123, Jun. 2001, pp. 264-269.
Kuo, A., Energetics of actively powered locomotion using the simplest walking model, Journal of Biomechanical Engineering, vol. 124, Feb. 2002, pp. 113-120.
LaFortune, Three-Dimensional Acceleration of the Tibia During Walking and Running, J. Biomechanics, vol. 24, No. 10, 1991, pp. 877-886.

(56) References Cited

OTHER PUBLICATIONS

LeBlanc, M. and Dapena, J., Generation and transfer of angular momentum in the javelin throw, Presented at the 20th annual meeting of the American Society of Biomechanics, Oct. 1996, Atlanta, Ga., pp. 17-19.
Lee et al., Activity and Location recognition Using Wearable Sensors, Pervasive Computing, Jul.-Sep. 2002, pp. 24-32.
Li et al., (Jun. 25, 2006) Research and development of the intelligently-controlled prosthetic ankle joint. Proc. of IEEE Int. Conf. on Mechatronics and Automation. Luoyang, China, pp. 1114-1119.
Light, et. al., Skeletal Transients on Heel Strike in Normal Walking With Different Footwear. J. Biomechanics vol. 13, pp. 477-480.
Liu, X., Low, K. H., Yu, H. Y., (2004) 'Development of a Lower Extremity Exoskeleton for Human performance Enhancement', IEEE Conf. on Intelligent Robots and Systems, Sendai, Japan.
Lloyd R. and Cooke C., Kinetic changes associated with load carriage using two rucksack designs, Ergonomics, vol. 43, No. 9, Sep. 2000, pp. 1331-1341.
Luinge, Inertial Sensing of Human Movement, Twente University Press, ISBN 9036518237, 2002, pp. 1-80.
Lundberg, A., Oct. 19, 1968. Reflex control of stepping. In: The Nansen memorial lecture V, Oslo: Universitetsforlaget, 5-42.
Maganaris, C., Force-length characteristics of in vivo human skeletal muscle, Acta Physiol. Scand., vol. 172, Aug. 2001, pp. 279-285.
Maganaris, C., Force-length characteristics of the in vivo human gastrocnemius muscle, Clin. Anat., vol. 16, May 2003, pp. 215-223.
Martens, W.L.J., Exploring the Information Content and Some Applications of Body Mounted Piezo-Resistive Accelerometers, in: P.H. Veltink and R.C. van Lummel (eds.), Dynamic Analysis using Body Fixed Sensors, ISBN 90-9007328-0, 1994, pp. 8-11.
Maufroy, C., Towards a general neural controller for quadrupedal locomotion, Neural Netw, vol. 21, No. 4, Apr. 2008, pp. 667-681.
Mayagoitia R., et al., Accelerometer and rate gyroscope measurement of kinematics: an inexpensive alternative to optical motion analysis systems, Journal of Biomechanics, vol. 35, Apr. 2002, pp. 537-542.
McFadyen et al., An integrated biomechanical analysis of normal stair ascent and descent. J Biomech. 1988;21(9):733-44.
McGeer T., Passive Dynamic Walking, International Journal of Robotics, vol. 9, No. 2, May 1988, pp. 62-82.
McGeer, T., Principles of walking and running, Advances in Comparative and Environmental Physiology, vol. 11, Ch. 4, Apr. 1992, pp. 113-139.
McIntosh, A., et. al., Gait dynamics on an inclined walkway, Journal of Biomechanics, vol. 39, Sep. 2005, pp. 2491-2502.
McMahon, T., et. al., Groucho Running, Journal of Applied Physiology, vol. 62, No. 6, Jun. 1987, pp. 2326-2337.
McMahon, T., The mechanics of running: how does stiffness couple with speed?, J. of Biomech., vol. 23, 1990, pp. 65-78.
Minassian, K., et. al., Human lumbar cord circuitries can be activated by extrinsic tonic input to generate locomotor-like activity, Hum. Mov. Sci., vol. 26, Mar. 2007, pp. 275-295.
Mochon, S., et. al., Ballistic walking, Journal of Biomechanics, vol. 13, Dec. 1980, pp. 49-57.
Moe-Nilssen, A new method for evaluating motor control in gait under real-life environmental conditions, Part 2: Gait analysis, Clinical biomechanics, vol. 13, 1998, pp. 328-335.
Molen, N., Energy/speed relation of below-knee amputees walking on motor-driven treadmill, Int. Z. Angew. Physio, vol. 31, Mar. 1973, pp. 173.
Morris, Accelerometry—A Technique for the Measurement of Human Body Movements, J. Biomechanics, vol. 6, Nov. 1973, pp. 729-736.
Muraoka, T., et. al, Muscle fiber and tendon length changes in the human vastus lateralis during slow pedaling, J. Appl. Physiol., vol. 91, Nov. 2001, pp. 2035-2040.
Nakagawa A., Intelligent Knee Mechanism and the Possibility to Apply the Principle to the Other Joints, Proceedings of the 20.sup.th Annual International Conference of the IEEE Engineering in Medicine and Biology Society, Vo. 20, No. 5, Oct. 1998,pp. 2282-2287.

Neal R. and Hinton G., A view of the EM algorithm that justifies incremental, sparse, and other variants, In Michael I. Jordan (editor), Learning in Graphical Models, 1999, Cambridge, MA, pp. 1-14.
Ng, et al., Fuzzy Model Identification for Classification of Gait Events in Paraplegics, IEEE Transactions on Fuzzy Systems, vol. 5, No. 4, Nov. 1997, pp. 536-544.
Nielsen, D., et. al., Comparison of energy cost and gait efficiency during ambulation in below-knee amputees using different prosthetic feet—a preliminary report, Journal of Prosthetics & Orthotics, vol. 1, No. 1, 1989, pp. 24-29.
Oda et al., In Vivo Length-Force Relationships on Muscle Fiber and Muscle Tendon Complex in the Tibialis Anterior Muscle. Int. J. Sport and Health Sci. 2005;3:245-252.
Ogihara, N. and Yama7aki, N., Generation of human bipedal locomotion by a bio-mimetic neuro-musculo-skeletal model, Biol Cybern, vol. 84, No. 1, Jan. 2001, pp. 1-11.
Palmer, M., Sagittal plane characterization of normal human ankle function across a range of walking gait speeds, Master's Thesis, MIT, Feb. 2002, Cambridge, MA, pp. 1-71.
Paluska, D. and Herr, H., Series Elasticity and Actuator Power Output, Proceedings of the 2006 IEEE International Conference on Robotics and Automation, May 2006, Orlando, FL, pp. 1830-1833.
Paluska, D., and Herr, H., The effect of series elasticity on actuator power and work output: implications for robotic and prosthetic joint design, Robotics and Autonomous Systems, vol. 54, Jun. 2006, pp. 667-673.
Pang, M., et. al., The initiation of the swing phase in human infant stepping: importance of hip position and leg loading, J Physiol, vol. 528, No. 2, Oct. 2000, pp. 389-404.
Pasch, K. A., and W. P. Seering, On the drive systems for high performance machines, AMSE J. Mechanisms, Transmissions, and Automation in Design vol. 106, pp. 102-108, Mar. 1984.
Paul, C., et. al., Development of a human neuro-musculo-skeletal model for investigation of spinal cord injury, Biol Cybern, vol. 93, No. 3, Aug. 2005, pp. 153-170.
Pearson, K., Generating the walking gait: role of sensory feedback, Prog Brain Res, vol. 143, 2004, pp. 123-129.
Perry, Gait Analysis: Normal and Pathological Function, New Jersey: SLACK Inc.; 1992, Book Review, 1 page.
Perry, J. and S. Shanfield, Efficiency of dynamic elastic response prosthetic feet, Journal of Rehabilitation Research and Development, vol. 30, No. 1, 1993 pp. 137-143.
Petrofsky et al., Feedback Control System for Walking in Man, Comput. Biol. Med., vol. 14, No. 2, Mar. 1984, pp. 135-149.
Pfeffer et al., Experiments with a Dual-Armed, Cooperative, Flexible-Drivetrain Robot System, Proc. 1993 IEEE Int. Conf. on Robotics & Automation, vol. 3, pp. 601-608, May 5, 1993.
Popovic D., et al., Control Aspects of Active Above-Knee Prosthesis, Int. Journal Man-Machine Studies, (1991) 35, pp. 751-767.
Popovic, D., Control of Movement for the Physically Disabled, Springer-Verlag London Limited, May 2000, pp. 270-302.
Popovic, et al., Gait Identification and Recognition Sensor, Proceedings of 6th Vienna International Workshop on Functional Electrostimulation, Sep. 1998, pp. 1-4.
Popovic, M. and Herr, H., Global Motion Control and Support Base Planning, Proceedings of the IEEE/RSJ International Conference on Intelligent Robots and Systems, Aug. 2005, Alberta, Canada, pp. 1-8.
Popovic, M., Angular Momentum Primitives for Human Walking: Biomechanics and Control, Proc. of the 2004 IEEE/RSJ International Conference on Intelligent Robots and Systems, Sep. 2004, Sendai, Japan., pp. 1685-1691.
Popovic, M., et. al., Angular Momentum Regulation during human walking: Biomechanics and Control, Proceedings of the 2004 IEEE International Conference on Robotics and Automation, Apr. 2004, New Orleans, LA, pp. 2405-2411.
Popovic, M., et. al., Ground Reference Points in Legged Locomotion: Definitions, Biological Trajectories and Control Implications, International Journal of Robotics Research, Dec. 2006, pp. 79-104.

(56) References Cited

OTHER PUBLICATIONS

Popovic, M., et. al., Zero spin angular momentum control: definition and applicability, Proceedings of the IEEE-RAS/RSJ International Conference on Humanoid Robots, Nov. 2004, Los Angeles, CA, pp. 1-16.
Popovic, M.B., W. Gu and H. Herr, Conservation of Angular Momentum in Human Movement, MIT AI Laboratory-Research Abstracts, Sep. 2002. pp. 231-232, 2002.
Pratt, G. and Williamson M., Series elastic actuators, Proceedings on IEEE/RSJ International Conference on Intelligent Robots and Systems, Jan. 1995, Pittsburgh, PA, pp. 399-406.
Pratt, G., Legged Robots: What's New Since Raibert, IEEE Robotics and Automation Magazine, Research Perspectives, Sep. 2000, pp. 15-19.
Pratt, G., Low Impedance Walking Robots, Integ. and Comp. Biol., vol. 42, Feb. 2002, pp. 174-181.
Pratt, J., et. al., The RoboKnee: An Exoskeleton for Enhancing Strength and Endurance During Walking, IEEE Conf. on Robotics and Automation, Apr. 2004, New Orleans, LA, pp. 2430-2435.
Prochazka, A. and Yakovenko, S., The neuromechanical tuning hypothesis, Prog Brain Res, vol. 165, Oct. 2007, pp. 255-265.
Prochazka, A., et. al., Positive force feedback control of muscles, J. of Neuro-phys., vol. 77, Jun. 1997, pp. 3226-3236.
Prochazka, A., et. al., Sensory control of locomotion: reflexes versus higher-level control, Adv Exp Med Biol, vol. 508, 2002, pp. 357-367.
Raibert, M., Legged Robots that Balance, The MIT Press, Nov. 1986, Cambridge, MA, p. 89.
Rassier, D., et. al., Length dependence of active force production in skeletal muscle, Journal of Applied Physiology, vol. 86, Issue 5, May 1999, pp. 1455-1457.
Reitman, et. al., Gait analysis in prosthetics: opinions, ideas and conclusions, Prosthetics and Orthotics International, 2002, 26, 50-57.
Riener, R., et. al., Stair ascent and descent at different inclinations, Gait Posture, vol. 15, Feb. 2002, pp. 32-44.
Robinson, D., Design and an analysis of series elasticity in closed-loop actuator force control, Ph.D. Thesis, MIT, Jun. 2000, Cambridge, MA, pp. 1-123.
Robinson, D., Series elastic actuator development for a biomimetic walking robot, Proceedings of IEEE/ASME International Conference on Advanced Intelligent Mechatronics, Sep. 1999, pp. 561-568.
Rosen, J., et al., A myosignal-based powered exoskeleton system, IEEE Transactions on Systems, Man, and Cybernetics—Part A: Systems and Humans, vol. 31, No. 3, May 2001, pp. 210-222.
Ruina, A., et. al., A collisional model of the energetic cost of support work qualitatively explains leg sequencing in walking and galloping, pseudo-elastic leg behavior in running and the walk-to-run transition, Journal of Theoretical Biology,vol. 237, Issue 2, Jun. 2005, pp. 170-192.
Rybak et al., Modelling spinal circuitry involved in locomotor pattern generation: insights from the effects of afferent stimulation. J Physiol. Dec. 1, 2006;577(Pt 2):641-58. Epub Sep. 28, 2006.
Rybak, I., et. al., Modelling spinal circuitry involved in locomotor pattern generation: insights from deletions during fictive locomotion, J Physiol, vol. 577 (Pt 2), Dec. 2001, 617-639.
Sanderson, D., et. al., Lower extremity kinematic and kinetic adaptations in unilateral below-knee amputees during walking, Gait and Posture, vol. 6, No. 2, Oct. 1997, pp. 126-136.
Sanger, T., Human arm movements described by a low-dimensional superposition of principal component, Journal of NeuroScience, vol. 20, No. 3, Feb. 2000, pp. 1066-1072.
Saranli, U., RHex: A simple and highly mobile hexapod robot, Int. Jour. Rob. Res., vol. 20, No. 7, Jul. 2001, pp. 616-631.
Sarrigeorgidis K. and Kyriakopoulos K., Motion control of the N.T.U.A. robotic snamek on a planar surface, Proc. of the 1998 IEEE International Conference on Robotics and Automation, May 1998, pp. 2977-2982.
Schaal, S. and Atkeson, C., Constructive incremental learning from only local information, Neural Computation, vol. 10, No. 8, Nov. 1998, pp. 2047-2084.
Schaal, S., Is imitation learning the route to humanoid robots? Trends in Cognitive Sciences, vol. 3, Jun. 1999, pp. 233-242.
Scott, S. and Winter, D., Biomechanical model of the human foot: kinematics and kinetics during the stance phase of walking, J. Biomech., vol. 26, No. 9, Sep. 1993, 1091-1104.
Sekine et al., Classification of waist-acceleration signals in a continuous walking record, Medical Engineering & Physics, vol. 22, 2000, pp. 285-291.
Sentis, L. and O. Khatib, Task-Oriented Control of Humanoid Robots Through Prioritization, IEEE-RAS/RSJ International Conference on Humanoid Robots, Nov. 2004, Santa Monica, CA, pp. 1-16.
Seyfarth, A., et. al., A movement criterion for running, J. of Biomech., vol. 35, May 2002, pp. 649-655.
Seyfarth, A., et. al., Stable operation of an elastic three-segmented leg, Biol.Cybern., vol. 84, 2001, pp. 365-382.
Seyfarth, A., Swing-leg retraction: a simple control model for stable running, J. Exp. Biol., vol. 206, Aug. 2003, pp. 2547-2555.
Sin et al., Significance of non-level walking on transtibial prosthesis fitting with particular reference to the effects of anterior-posterior alignment, Journal of Rehabilitation Research and Development, vol. 38, No. 1, Jan./Feb. 2001, p. 1-6.
Sinkjaer, T., et. al., Major role for sensory feedback in soleus EMG activity in the stance phase of walking in man, J Physiol, vol. 523, No. 3, Mar. 2000, 817-827.
Skinner, H. and Effeney D., Gait analysis in amputees, Am J Phys Med, vol. 64, Apr. 1985, pp. 82-89.
Smidt et al., An Automated Accelerometry System for Gait Analysis, J. Biomechanics, vol. 10, 1977, pp. 367-375.
Srinivasan, M., Energetics of legged locomotion: Why is total metabolic cost proportional to the cost of stance work, Proc. on ISB XXth Congress and the American Society of Biomechanics Annual Meeting, Jul. 2003, Cleveland, OH, pp. 829.
Stepien, J., et al., Activity Levels Among Lower-Limb Amputees: Self-Report Versus Step Activity Monitor, Arch. Phys. Med. Rehabil., vol. 88, No. 7, Jul. 2007, pp. 896-900.
Sugano et al., Force Control of the Robot Finger Joint equipped with Mechanical Compliance Adjuster, Proc. of the 1992 IEEE/RSJ Int. Conf. on Intell. Robots & Sys., Jul. 1992, pp. 2005-2013.
Sugihara, T., et. al., Realtime Humanoid Motion Generation through ZMP Manipulation based on Inverted Pendulum Control, Proceedings of the 2002 IEEE International Conference on Robotics and Automation, May 2002, Washington, DC, pp. 1404-1409.
Sup, F., Design and Control of a Powered Transfemoral Prosthesis, The International Journal of Robotics Research, vol. 27, No. 2, Feb. 2008, pp. 263-273.
Taga, G., A model of the neuro-musculo-skeletal system for human locomotion, Biol. Cybern., vol. 73, No. 2, Jul. 1995, pp. 97-111.
Takayuki, Biped Locomotion using Multiple Link Virtual Inverted Pendulum Model, Publication of Electronics Information and Systems Society, vol. 120, No. 2, Feb. 2000, 8 pages.
Thoroughman, K. and R. Shadmehr, Learning of action through adaptive combination of motor primitives, Nature, vol. 407, Oct. 2000, pp. 742-747.
Tomovic R. et al., A Finite State Approach to the Synthesis of Bioengineering Control Systems, IEEE Transations on Human Factors in Electronics, vol. 7, No. 2, Jun. 1966, pp. 65-69.
Tong et al., Virtual artificial sensor technique for functional electricial stimulation, Medical Engineering & Physics, vol. 20, 1998, pp. 458-468.
Tong, et al., A Practical Gait Analysis System Using Gyroscopes, Medical Engineering & Physics, vol. 21, Mar. 1999, pp. 87-94.
Turker, K., Electromyography: some methodological problems and issues, Physical Therapy, vol. 73, No. 10, Oct. 1993, pp. 698-710.
van den Bogert, A., Exotendons for assistance of human locomotion, Biomedical Engineering Online, Oct. 2003, pp. 1-8.
van den Bogert, et al. A Method for Inverse Dynamic Analysis Using Accelerometry, Journal Biomechanics, vol. 29, No. 7, 1996, pp. 949-954.

(56) References Cited

OTHER PUBLICATIONS van der Kooij et al., A multisensory integration model of human stance control, Biological Cybernetics, 1999, pp. 299-308.
Veltink P., et al., The Feasibility of Posture and Movement Detection by Accelerometry, D-7803-1377-I/93, IEEE, Oct. 1993, pp. 1230-1231.
Veltink, Dection of Static and Dynamic Activities Using Uniaxial Accelerometers, IEEE. Transactions on Biomedical Engineering, vol. 4. No. 4, Dec. 1996, pp. 375-385.
Vukobratovic M. and Juricic, D., Contributions to the synthesis of biped gait, IEEE Transactions on Biomedical Engineering, vol. BME-16, No. 1, Jan. 1969, pp. 1-6.
Vukobratovic M. and Stepanenko J., Mathematical models of general anthropomorphic systems, Mathematical Biosciences, vol. 17, Aug. 1973, pp. 191-242.
Walsh, C., Biomimetic Design of an Under-Actuated Leg Exoskeleton for Load-Carrying Augmentation, Master's Thesis, MIT, Feb. 2006, pp. 1-94.
Waters, RL., Energy cost of walking amputees: the influence of level of amputation, J Bone Joint Surg., vol. 58, No. 1, Jan. 1976, pp. 42-46.
Wilkenfeld, A. J., Biologically inspired auto adaptive control of a knee prosthesis, Ph.D. Thesis, Massachusetts Institute of Technology, Oct. 23, 2000.
Wilkenfeld, A., An Auto-Adaptive External Knee Prosthesis, Artificial Intelligence Laboratory, MIT, Sep. 2000, Cambridge, MA, pp. 1-3.
Willemsen A., et al., Automatic Stance-Swing Phase Detection from Accelerometer Data for Peroneal Nerve Stimulation, IEEE Transactions on Human Factors in Electronics, vol. 37, No. 12, Dec. 1990, pp. 1201-1208.
Willemsen A., et al., Real-Time Gait Assessment Utilizing a New Way of Accelerometry, Journal of Biomechanics, vol. 23, No. 8, 1990, pp. 859-863.

Williams, B., Mode Estimation of Model-based Programs: Monitoring Systems with Complex Behavior, Proceedings of the International Joint Conference on Artificial Intelligence, Aug. 2001, Seattle, WA, pp. 1-7.
Williamson, M., Series Elastic Actuators, Artificial Intelligence Laboratory, MIT, Jan. 1995, Cambridge, MA, pp. 1-74.
Winter, D, and Robertson D., Joint torque and energy patterns in normal gait, Biol. Cybem., vol. 29, May 1978, pp. 137-142.
Winter, D. A, Energy generation and absorption at the ankle and knee during fast, natural, and slow cadences, Clinical Orthopedics and Related Research, vol. 175, May 1983, pp. 147-154.
Winter, D. and Sienko S., Biomechanics of below-knee amputee gait, Journal of Biomechanics, vol. 21, No. 5, Aug. 1988, pp. 361-367.
Wisse, M., Essentails of Dynamic Walking, Analysis and Design of two-legged robots, Phd Thesis, Technical University of Delft, 2004, pp. 1-195.
Woodward et al., Skeletal Accelerations measured during different Exercises, Proceedings of the Institution of Mechanical Engineers, Part H: Journal of Engineering in Medicine, vol. 207, Jun. 1993, pp. 79-85.
Wu, The Study of Kinematic Transients in Locomotion Using the Integrated Kinematic Sensor, IEEE Transactions on Rehabilitation Engineering, vol. 4, No. 3, Sep. 1996, p. 193-200.
Yakovenko, S., et. al., Contribution of stretch reflexes to locomotor control: a modeling study, Biol Cybern, vol. 90, No. 2, Jan. 2004, pp. 146-155.
Yun X., Dynamic state feedback control of constrained robot manipulators, Proc. of the 27th conference on Decision and Control, Dec. 1988, pp. 622-626.
Zlatnik, D., et al., Finite-state control of a trans-femoral prostheis, IEEE Tran. on Control System Technology, vol. 10, No. 3, May 2002, pp. 408-420.

\* cited by examiner

SIGNALS ASSOCIATED WITH THE MOTOR AND JOINT SYSTEM

CURRENT FEEDBACK LOOP

DIRECT CONTROL OF JOINT TORQUE

EMF FEEDFORWARD WITH CURRENT FEEDBACK LOOP

EMF FEEDFORWARD WITH JOINT TORQUE FEEDBACK LOOP

BLOCK DIAGRAM. Eqs. (9) - (12)

INNER LOOP CLOSED

EMF FEEDFORWARD

SINGLE CONTROL LOOP ON JOINT TORQUE

INNER LOOP ON MOTOR CURRENT
WITH OUTER LOOP ON JOINT TORQUE

BIOMIMETIC TRANSFEMORAL PROSTHESIS

RELATED APPLICATIONS

This application is a national stage filing under 35 U.S.C. §371 of international PCT application PCT/US2012/063395, filed on Nov. 2, 2012, which claims priority to and the benefit of U.S. Provisional Patent Application Ser. No. 61/554,921 filed on Nov. 2, 2011, the disclosure of which is hereby incorporated herein by reference in its entirety. The application also relates to U.S. Pat. No. 8,075,633, U.S. patent application Ser. Nos. 12/551,845, 12/552,013, 12/552,021, 12/552,028, 12/552,036, 12/872,425, 13/079,564, 13/079,571, 13/347,443, 13/349,216, 13/356,230, and 13/417,949, and U.S. Provisional Patent Application Nos. 61/554,921, 61/595,453, 61/658,568, 61/659,729, 61/662,104, 61/649,640, 61/659,723, 61/679,194, and 61/691,684, the disclosures of which are each hereby incorporated herein by reference in their entireties.

FIELD OF THE INVENTION

This invention relates generally to systems and methods for lower body locomotion, and more particularly to the control of prosthetic, orthotic, and exoskeleton devices usable at various points of the leg, including the ankle, knee, and hip.

BACKGROUND

Over 120,000 people suffer lower-extremity amputations each year in the United States, of which transfemoral (above-knee) amputations account for over 40%. Over 30,000 people in this transfemoral population require a new prosthetic limb each year—typically a passive, microprocessor-controlled knee joint, employing hydraulic damping and a passive carbon-fiber ankle-foot prosthesis. Such passive leg systems tend not to be biomimetic; instead they tend to be passive-elastic during stance and can neither perform net non-conservative work to propel the amputee upward and forward nor deliver the temporal torque response supplied by an intact knee and ankle joint during the gait cycle, and hence fail to fully restore function when integrated onto the residual limb. Researchers have hypothesized that the inability of conventional passive-elastic ankle-foot prostheses to provide sufficient positive power at terminal stance to limit heel strike losses of the adjacent leg is a key mechanism for the increased metabolic rate of walking amputees. These limitations in both ankle-foot and knee designs contribute to the severity of clinical problems experienced by transfemoral amputees.

Current leg prostheses tend not to provide the balance desired by the transfemoral community. Amputees often fall, especially while traversing rough or irregular terrain. This may be at least partially due because most ankle-foot prostheses fail to actively control a zero-moment point (ZMP) at the foot-ground interface, a balancing strategy sometimes employed in the field of humanoid robotics. In addition to balance problems, amputees tend to tire easier and walk slower than non-amputees. For example, amputees can require 10-60% more metabolic energy to walk than intact persons. The actual differences for any individual at a particular time result from differences in walking speed, physical fitness level, cause of amputation, level of amputation, and prosthetic intervention characteristics. Amputees may walk at much slower (e.g., 11-40%) self-selected gait speeds than do persons with intact limbs.

Integration of non-biomimetic ankle-foot and microprocessor-controlled knee prostheses has confounded researchers. Although some improvements in gait have been observed with variable-damper knee designs, many problems still remain for transfemoral amputees. For example, a variable-damper knee combined with a passive-elastic ankle-foot prosthesis offers little to no improvement in gait metabolism and walking speed compared to a mechanically-passive transfemoral system. Although some powered knee systems have been developed, these tend not to be biomechanically-conceived, and can take hours to fit and tune to a specific wearer. These powered knees tend to have a noisy motor and transmission system. Other powered robotic leg systems often exhibit three fundamental limitations: inefficient actuator design, non-biomimetic actuator control software, and poorly executed terrain-adaptation software. Without a biologically-conceived actuator, the motor must be made larger and heavier to deliver necessary joint powers.

To deliver the increased power, high gear-ratio transmissions are normally employed in powered leg prosthetic and orthotic applications, driven by high RPM brushless motors that are operated at currents in excess of 10× the rated current. The result is often a noisy transmission that dissipates battery power excessively, heating the motor windings instead of applying power to the joint. As a result, batteries must be made larger than necessary, or else the range on a battery charge is compromised unnecessarily. Further, motor heating can be excessive when extended periods of walking (e.g., hundreds of steps consecutively) are applied. The useful range of the prosthesis may be constrained by the need to "fold back" power when the motor windings get too hot. Most robots are programmed explicitly in a position-controlled or playback mode. Biophysically-conceived robots employ mono-articular and biarticular bionic muscle-tendon units that modulate joint impedance, equilibrium, torque and positive-feedback reflex during a gait cycle. The behavior of these bionic systems can be encoded in a relatively few parameters, implicitly defined rather than explicitly defined. Indeed, only a few parameters need to be changed to emulate biological behavior. In contrast, the explicitly controlled systems often require that movement as defined by joint angle trajectories is tuned to match biological behavior to create a response for every special case, driven by speed, terrain modality and wearer athleticism/payload. Even the most experienced clinicians may be unable to set up such a system. While many current robotic leg prostheses employ inertial componentry to estimate terrain modality, these are usually configured to adapt to the new terrain modality after several steps, whereas an intact person adjusts to terrain modality within each step. Though certain implementations of such a control may rely on playing back a temporal response at a particular terrain state, the desired behavior can be virtually impossible to tune.

It is therefore desirable to provide leg devices that provide a biomimetic response throughout a walking cycle.

SUMMARY OF THE INVENTION

Lower-extremity augmentation may rely on a muscle-tendon architecture employing series-elasticity as a means of amplifying available joint power, reducing motor work, and improving shock tolerance. An intact ankle-foot for instance employs a series-elastic actuator in the form of the calf muscle (motor) driving through the Achilles tendon (series-elasticity). A model of an intact human ankle progressing through various phases of a gait cycle is depicted in FIG. 1. Elastic energy is stored in the tendon in the controlled dorsiflexion phase and released later, like a catapult, in powered plantar flexion to augment the power applied by the calf muscle. A series elastic actuator (SEA) as described herein can provide a biomimetic response, and may be capable of amplifying power by greater than a factor of two.

A transfemoral prosthesis may include the SEA, motor technology, neuromuscular-inspired actuator control, and intrinsic inertial sensing to provide quiet and efficient biomimetic mechanical behaviors across distinct walking speeds and terrains and the transitions between these ground surfaces. The prosthesis can provide the amputee with an enhanced metabolic economy when using a powered, ankle-foot prosthesis compared to the metabolic cost when using a conventional passive-elastic prosthesis, including a normalization of self-selected walking speed and improvement in metabolic cost-of-transport across a broad walking speed range (0.75-1.75 m/sec) using sensing, control and muscle-tendon unit (MTU) actuators.

The prosthesis may integrate an artificial MTU that employs a high-torque, transverse-flux motor that reduces, in some instances over an order of magnitude, the normalized motor copper loss, $$\frac{R}{k_t^2},$$

in relation to conventional, radial flux motor topologies employed in the many existing robotic augmentation devices. The use of a direct-drive, transverse flux motor in an MTU may result in a much lower drive transmission ratio (e.g., six times lower than a typical 200:1 gear-ratio transmission of a typical motor), allowing for operation at lower motor RPM to provide a more quiet and efficient device. Another result may be a higher resonant frequency for the MTU, allowing for higher fidelity joint torque control.

The device may also include neuromuscular-inspired control software to emulate the biological response of an intact limb, aiding in the normalization of metabolic walking economy and biomechanical response. Intrinsic inertial sensing can enable in-situ, real-time reconstruction of hip, knee and ankle trajectory throughout the gait cycle. Pattern recognition algorithms may be applied to these reconstructed trajectories for intra-step terrain discrimination and adaptation, thereby enabling seamless terrain transitions across walking speeds.

A wearer of the biomimetic prosthesis may experience an improved walking speed, metabolic economy, gait symmetry, and gait stability across level, sloped, and stair ground surfaces when compared to conventional prostheses. This restored function by objective metabolic and biomechanical measures can provide profound improvements in the quality of life of a wearer. While the device is often described with respect to a prosthetic for an amputee population, the robotic augmentation platform described here may be useful to researchers and educators focused on humanoid robots. Open interfaces may be provided to configure, refine, and deploy new applications.

According to one aspect, the invention relates to a method for controlling a motorized, artificial limb having an actuator. The actuator includes a motor coupled in series with an elastic element to apply a torque characteristic to a joint. The method includes applying a voltage to windings of the motor, measuring the torque characteristic at the joint, computing a torque characteristic error as a difference between a target torque characteristic and the measured torque characteristic, and controlling the applied voltage independently of motor current to reduce the torque characteristic error.

In some embodiments, the torque characteristic is a joint torque, a joint impedance, or a joint equilibrium. The applied voltage may be controlled solely based on the target torque characteristic and the torque-characteristic error. In certain embodiments, the controlling step avoids computation of motor current and/or computation of an adjustment to the motor current supplied to the motor to achieve the target torque characteristic, and may avoid measurement of motor current and using the measured current for adjusting the motor current (at least in part).

In other embodiments, the limb control method is independent of a resonance frequency associated with the coupling of the motor and the elastic element. The step of measuring the torque characteristic at the joint may include measuring an angular position of the motor and/or an angular position of the joint. The method may also include measuring motor speed, estimating voltage corresponding to back electromotive force related to the motor speed, and controlling the applied voltage based on, at least in part, the estimated voltage corresponding to the back electromotive force. In certain embodiments, the artificial limb is a prosthetic limb and/or an orthotic limb. The joint may be an ankle joint or a knee joint.

In another aspect, the invention relates to an artificial limb system. The system includes an actuator coupled to a joint for applying a torque characteristic thereto, the actuator having a motor coupled in series with an elastic element. The system also includes a power source for applying a voltage to windings of the motor, at least one sensor for estimating the torque characteristic at the joint, and a controller for: (i) computing a torque characteristic error as a difference between a target torque characteristic and the torque characteristic measured by the sensor, and (ii) controlling the applied voltage independently of motor current, to reduce the torque characteristic error.

In some embodiments, the torque characteristic comprises a joint torque, a joint impedance, and/or a joint equilibrium. The controller may be adapted for controlling the applied voltage solely based on the target torque characteristic and the torque-characteristic error. In other embodiments, the controller is adapted for controlling the applied voltage without using a computation of motor current and/or an adjustment to the motor current supplied to the motor to achieve the target torque characteristic. The controller may be adapted to avoid at least partially using a measurement of motor current for an adjustment thereof. The controller may be adapted such that a controller response is independent of a resonance frequency associated with the coupling of the motor and the elastic element.

In certain embodiments, the artificial limb system is a prosthetic limb system and/or an orthotic limb system. The joint may be an ankle joint or a knee joint. The sensor may be a joint encoder, a torque sensor, a deflection sensor disposed on the series elastic element, a joint angle sensor, or a motor angle sensor. In some embodiments the system includes a motor encoder for measuring motor speed with the controller adapted to: (i) estimate voltage corresponding to back electromotive force related to the motor speed, and (ii) control the applied voltage based on, at least in part, the estimated voltage corresponding to the back electromotive force. The system may include an observer to estimate voltage corresponding to back electromotive force with the controller adapted to control the applied voltage based on, at least in part, the estimated voltage corresponding to the back electromotive force. The system may include a linkage having a plurality of links where the linkage is coupled to the joint, the motor is coupled to a first link in the linkage, and the elastic element is coupled to a second link in the linkage.

In yet another aspect, the invention relates to a method for controlling a motorized, artificial limb. The artificial limb has an actuator with a motor coupled in series with an elastic element to apply a torque characteristic to a joint. The method includes computing target motor current required to achieve substantially a target torque characteristic at the joint, measuring motor current and motor speed, and computing a current error as a difference between the target motor current and the measured motor current. The method also includes estimating voltage corresponding to back electromotive force related to the motor speed and controlling voltage applied to motor windings based on, at least in part, (i) the estimated voltage corresponding to the back electromotive force, and (ii) the current error, to reduce the current error.

In certain embodiments, the torque characteristic is a joint torque, a joint impedance, and/or a joint equilibrium. The artificial limb may be a prosthetic limb and/or an orthotic limb. The joint may be an ankle joint, a knee joint, and a hip joint.

In still another aspect, the invention relates to an artificial limb system. The system includes an actuator with a motor coupled in series with an elastic element coupled to a joint for applying a torque characteristic, a power source for applying a voltage to windings of the motor, a current sensor for measuring motor current, and a motor encoder for measuring motor speed. The system also includes a controller for computing a current error as a difference between a target current and the measured motor current, estimating voltage corresponding to back electromotive force related to the measured motor speed, and controlling voltage applied to motor windings based on, at least in part, (i) the estimated voltage corresponding to the back electromotive force, and (ii) the current error, to reduce the current error.

In some embodiments, the artificial limb system is a prosthetic limb system and/or an orthotic limb system. The joint may be an ankle joint, a knee joint, or a hip joint. The controller may be adapted to determine the target motor current to achieve the target joint torque characteristic.

BRIEF DESCRIPTION OF THE FIGURES

Other features and advantages of the present invention, as well as the invention itself, can be more fully understood from the following description of the various embodiments, when read together with the accompanying drawings, in which.

DETAILED DESCRIPTION

Devices for transfemoral amputees typically include at least a foot-ankle device and a knee device. The foot-ankle and knee devices described herein may be used together or separately, particularly only a foot-ankle device for below-knee amputees. While the embodiments described relate to prostheses, the concepts contained herein may also be useful in other applications, including orthoses and exoskeletons.

Figure 1:
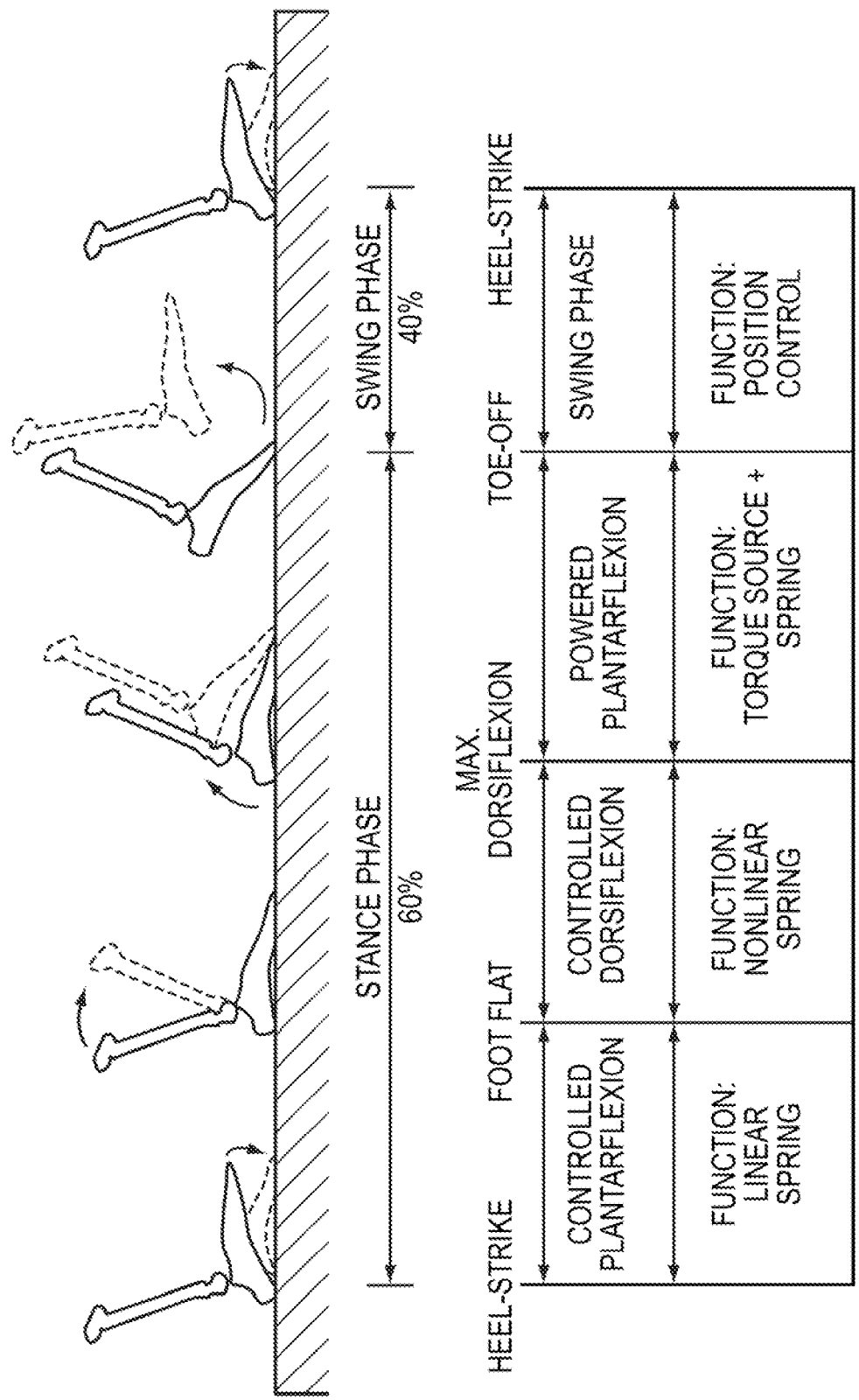
FIG. 1 is a diagram of a healthy ankle throughout the phases of a walking cycle.
Figure 2:
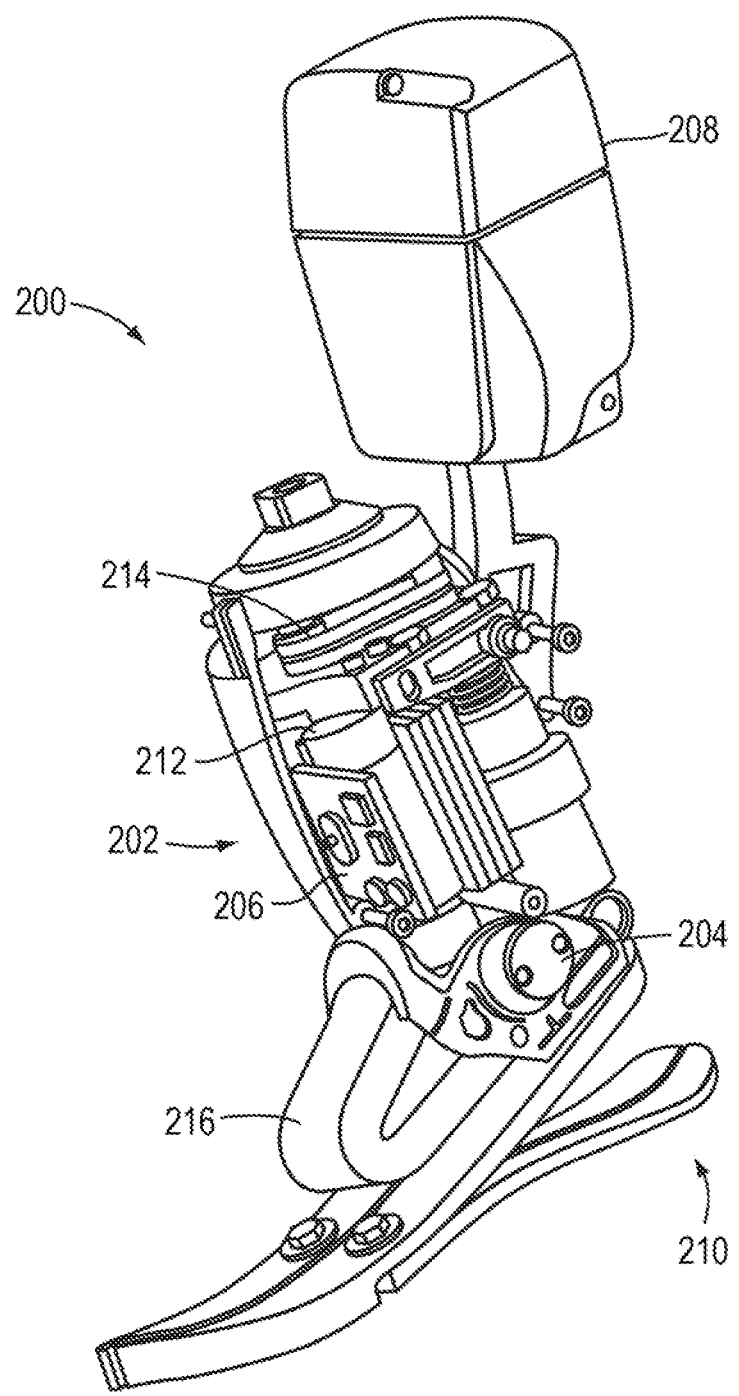
FIG. 2 is a schematic perspective view of an ankle device, in accordance with one embodiment of the invention.

One ankle device 200 capable of restoring ankle function as defined by objective metabolic and biomechanical measures is depicted in FIG. 2. The ankle device 200 is capable of varying ankle impedance during the early to mid-stance periods of walking, emulating the quasi-static stiffness of an intact biological ankle. In addition, the prosthesis 200 provides a sufficiently large instantaneous power output and torque to propel an amputee upward and forward during powered plantar flexion, while still matching the size and weight of an intact ankle-foot complex, e.g., approximately 2.4% of body weight. The ankle device 200 may be a variety of weights for different applications. For example, a device 200 weighing approximately 4.8 lbs is appropriate for wearers weighing approximately 190-250 lbs.

Figure 3:
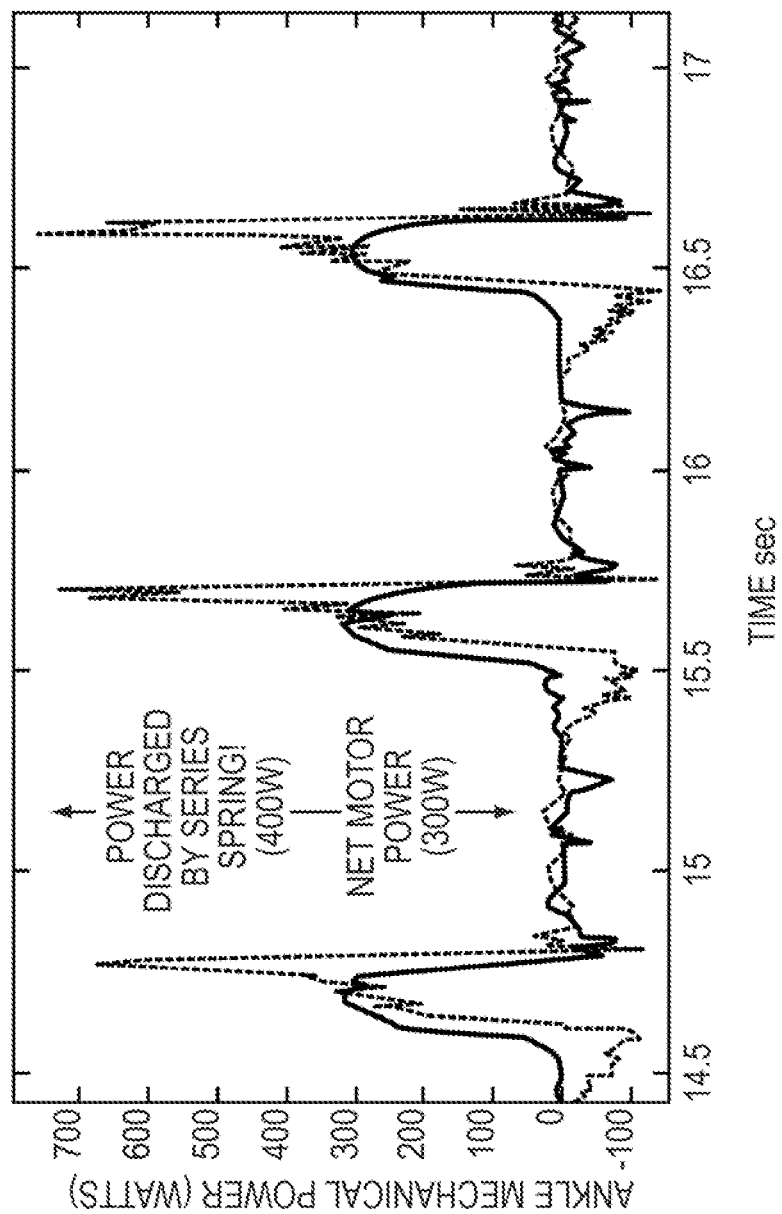
FIG. 3 is a graph depicting the power output of the ankle device, in accordance with one embodiment of the invention.

The ankle device 200 may include several different technologies, including a series-elastic actuator (SEA) 202, integral joint torque sensor 204, six degree-of-freedom inertial measurement unit (IMU) 206, battery 208, and a controller with control firmware 210 (intrinsic within the system). The SEA 202 is capable of modulating torque, impedance and position in accordance with the gait cycle state. Such may be nuanced as a function of sensed walking speed and terrain modality. Through use of the intrinsic control firmware 210, the SEA 202 may emulate the calf muscle/Achilles tendon reflex during late stance to achieve biomimetic operation. The SEA 202 design may be optimized to amplify peak joint mechanical output power, e.g., $2\times^+$ amplification during fast walking, as illustrated in FIG. 3. The SEA 202 may have a high-RPM brushless motor 212, a hybrid belt/ball-screw transmission 214, and a carbon-fiber spring 216. The transmission 214 can have an L1 design life of greater than 5 million cycles, and the SEA 202 may operate at an overall motor-joint gear ratio of about 220:1.

The joint torque sensor 204 may be used to precisely sense joint angle and SEA motor 212 position. The joint torque may be computed in real-time using factory calibrated models of ankle shell and carbon-fiber spring deflection, even without strain measurement devices. The IMU 206 may measure angular rate and acceleration in each of three orthogonally-opposed directions. These measures may be used selectively to detect gait cycle state transitions and instantaneous walking speed. The battery 208 is used to power the device, and may be modular to aid in insertion and removal. This is particularly helpful when the battery 208 is replaced multiple times in a day, e.g., two to three times. Many different types of batteries 208 may be used, including a lithium polymer battery.

The control firmware 210 may rely on a state machine for transitioning between various control schemes based on the phase of gait. Sensors may be used to sense the transitions while walking. For example, the firmware 210 can use intrinsic sensing to track gait cycle transitions—enabling appropriate modulation of torque (including SEA reflex), impedance and position. The device 200 may employ nonlinear, positive torque feedback to simulate muscle response. This can provide a wearer with a natural (biomimetic) feel. Other models, e.g., a neuromuscular muscle model, may be used.

These component technologies may be used separately or in conjunction with each other, with several possible alterations for each. For example, the SEA 202 may have a transverse-flux motor 212 that eliminates the belt transmission 214, instead relying on a direct-drive ball-screw implementation that can reduce the gear ratio (e.g., by a factor of six). Power consumption may be reduced (in some cases by more than 50%), and acoustic noise in the 1.5-3 kHz band may be reduce by up to, and sometimes greater than, 80%.

Figure 4:
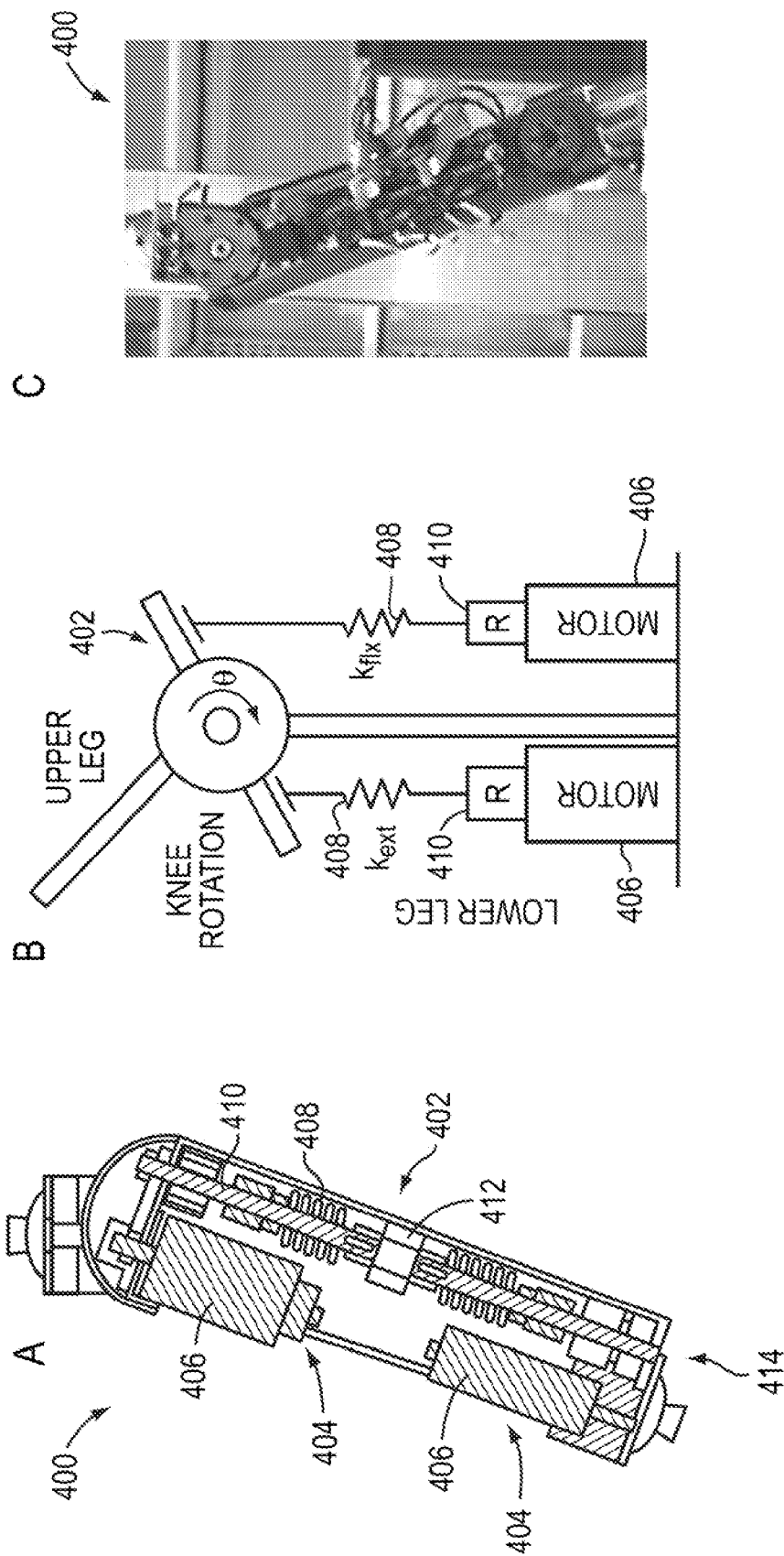
FIG. 4A is a schematic cross-section view of a knee device, in accordance with one embodiment of the invention.
FIG. 4B is a schematic diagram of the knee device of FIG. 4A.
FIG. 4C is a schematic side view of the knee device of FIG. 4A.

Powered prosthetic knees may use a variety of different components in different arrangements. In one embodiment, a prosthetic knee 400 depicted in FIGS. 4A-4C provides a biomimetic response through the use of an agonist-antagonist actuator (AAA) system 402. The AAA-based knee prosthesis 400 may emulate the synergistic muscle activity of an intact limb by using a dual-SEA system 402 that resembles the major mono-articular muscle groups that flex and extend the human knee joint. Each SEA 404 includes a torque source 406 (e.g., a motor), an elastic element 408 (e.g., a spring) in series with the torque source 406, and a transmission 410 (e.g., a ballscrew and ballnut drive). In some embodiments, the SEA 404, along with additional torque sensing, inertial sensing, and intrinsic control, may be the same or similar to those used in the ankle device 200, adapted for use in the knee 400 when necessary. A floating point 412 may be coupled to an upper leg attachment for the knee 400.

Figure 5:
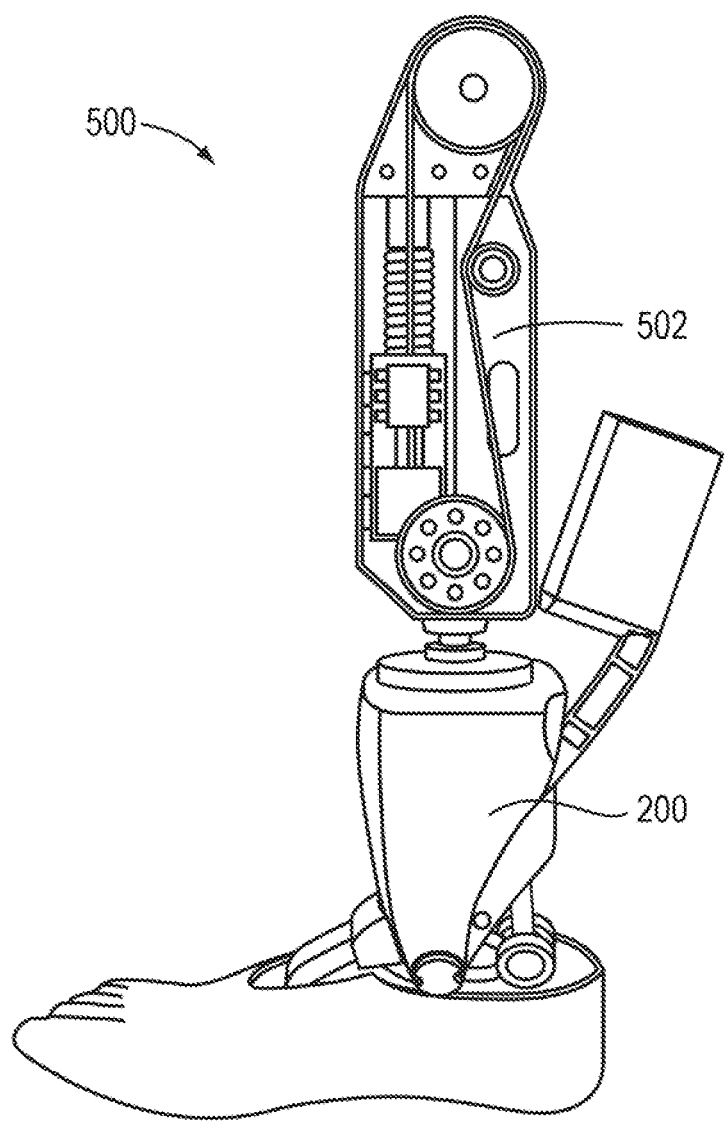
FIG. 5 is a schematic side view of a leg device, in accordance with one embodiment of the invention.

The mechanical architecture of the AAA knee 400 allows for independent engagement of flexion and extension tendon-like, series springs 408 for modulating joint impedance and non-conservative motive power during the stance period, and joint position when the prosthetic foot is off the ground. Furthermore, this architecture may permit joint rotation with near zero friction via disengagement of both SEAs 404, allowing a controller 414 (that may be intrinsic to the system) to take advantage of the passive (ballistic) dynamics of the system 402 in the swing phase, and thus, augment the overall energetic economy of the prosthesis 400 and human wearer. By matching the stiffness of the two series springs 408 to match the biomechanical extension and flexion stiffness, modulation of the stiffness can be accomplished with approximately zero-electrical power by simply shorting the motor windings (to apply a high-degree of damping and holding torque) of the appropriate motor 406. The clutching feature can be utilized to great advantage in a transverse-flux motor implementation due to the transverse-flux motors' superior brake/clutch performance resulting from its low motor resistance, $R_m$, in relation to the motor torque constant, $R_m/k_t^2$, which defines the motor damping with shorted leads. Certain embodiments of the knee prosthesis 400 may have a single motor with bilateral spring elements that can be always fully engaged as in a traditional SEA, or can be configured to have a "dead zone" in which neither spring is engaged, enabling agonist-antagonist "clutch" implementations. A leg prosthesis 500 including the ankle device 200 and a knee device 502 (similar to the knee device 400) coupled together is depicted in FIG. 5.

Figures 6A, 6B:
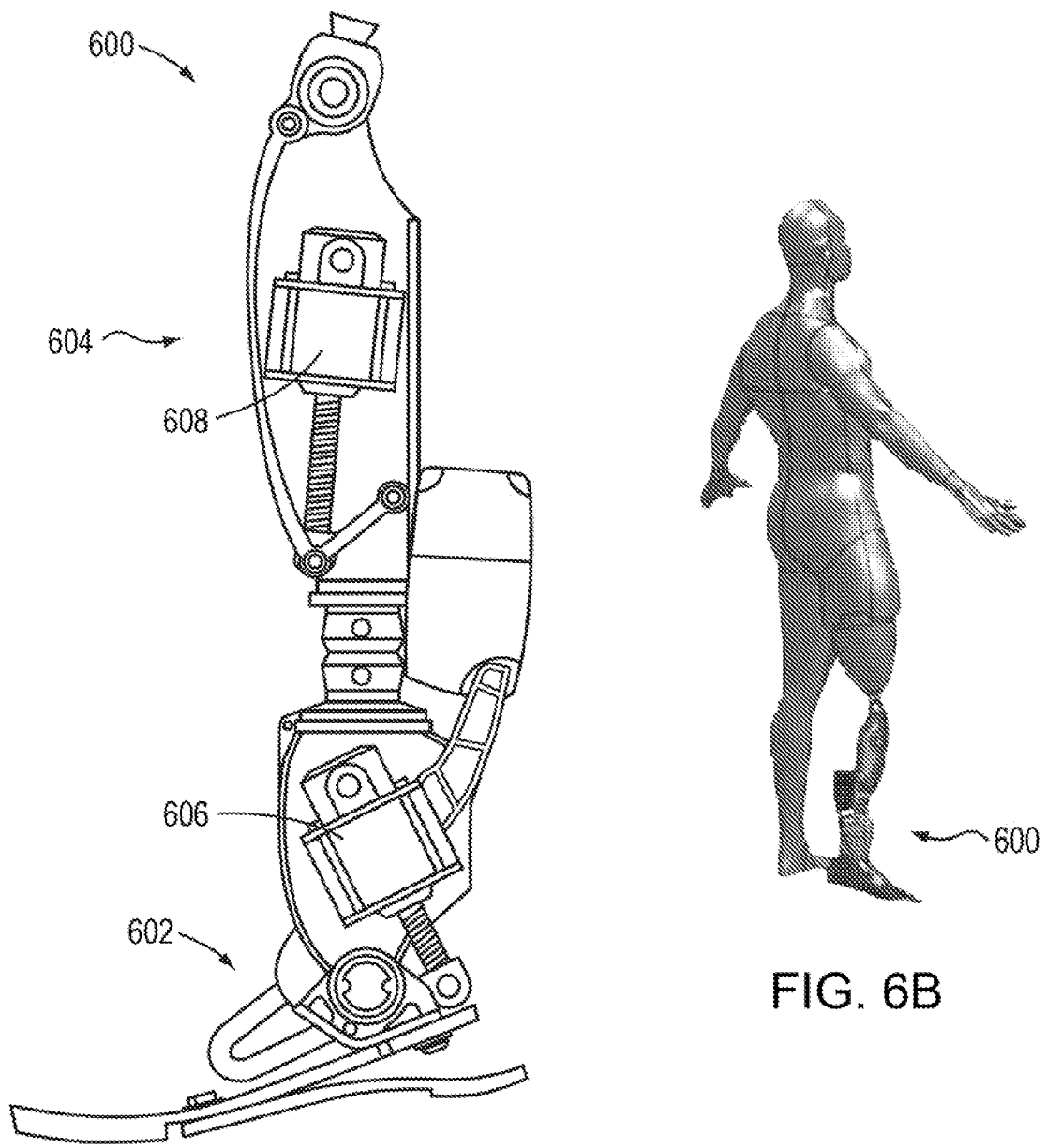
FIGS. 6A and 6B are schematic cross-section and rear perspective views, respectively, of a leg device in accordance with another embodiment of the invention.

Another embodiment of a leg prosthesis 600 is depicted in FIGS. 6A and 6B. The substantially fully-powered transfemoral prosthesis 600 may have a transverse flux, series-elastic ankle 602 and knee 603 to produce biological ankle and knee mechanics for steady-state level-ground walking with a prosthetic mass, shape and acoustic noise output comparable to a biological leg. For example, the prosthesis may have a mass<5% body weight, a shape smaller than a 50% person, and an acoustic output of <45 dB one meter from the prosthesis. Such a transfemoral prosthesis 600 may normalize metabolic economy and self-selected walking speed during ground surface ambulation in a variety of contexts, including during level-ground, sloped (e.g., up to ±10 degrees and beyond), stair ascent, stair descent, and transitions therebetween. The prosthesis 600 may be able to adapt ankle and knee mechanics within a single walking cycle to enable a transfemoral amputee to walk across these ground surface variations in a manner that emulates biological leg biomechanics.

The ankle device 602 may be substantially similar to the ankle device 200, with a transverse flux motor 606 used instead of a belt transmission. Using biomimetic, muscle-tendon-like actuators (e.g., SEAs) that employ such high-torque transverse flux motors 606 can help reduce power consumption and acoustic noise levels by significant amounts (e.g., over 50% and 80% respectively) when compared to conventional (radial flux) motor transmissions to achieve cool, quiet operation across substantially all walking speeds. High-torque transverse flux motors 606 may be available from Electric Torque Machines (Flagstaff, Ariz.). Another benefit of transverse-flux motor technology is the reduction of motor copper loss per square unit of torque production ($R/k_t^2$), which may be over a factor of nearly 300 at the same gear ratio as would be employed by conventional high-RPM radial flux motors like the EC30 PowerMax motor (www.maxon.com) used in most lower-extremity augmentation systems built by the research community. This attenuation in loss can be used to reduce both transmission gear ratio (and hence motor rotational speed) and motor temperature rise. The result is quiet and efficient operation that extends range on a battery charge and reduces or eliminates heating-related range limitations. Actuator design life may be extended because friction and travel are reduced in concert with gear ratio reduction.

The knee device (or muscle tendon unit; "MTU") 604 may employ a "buckled-beam" SEA design with a gear ratio, in this embodiment approximately 30:1. The buckled beam can be light-weight and yet store up to 30 J/kg (or more) of energy, enough suitable for running jumping. In some embodiments, the buckled-beam SEA may have a stiffness of approximately 4 Nm/rad/kg and energy storage of approximately 8 J/kg for level ground walking. The buckled-beam SEA may also use the transverse flux motor 606 as a dynamic brake (e.g., a clutch) in early stance flexion to reduce battery energy consumption and acoustic emissions.

The prosthesis 600 may have multiple MTU's (e.g., the ankle device 602 and the knee device 604), each with embedded SEA power electronics and servo controller(s) integrated onto the motor, networked to a State Controller/IMU assembly adapted to control and coordinate the individual MTU's in accordance with the gait cycle and terrain modality. Connectivity among the remote components may be accomplished through the use of wireless technologies, such as Bluetooth® and smart WiFi (sWiFi) control modules. A BlueTooth) port can enable remote programming by Android-based cell phone/PDA to facilitate clinical tuning and evaluation. The sWiFi may be used to promote 500 Hz logging of up to 50 floating point-state variables, enabling a modification of up to 200 (and greater) control and signal processing parameters while the biomimetic prosthesis is in use.

The MTUs 602, 604 may be designed around biomechanical torque-displacement trajectories to ensure the MTUs 602, 604 can provide a biomimetic response. Through the design process, certain targets may be set, such as battery and motor power electronic requirements. In one instance, the components may be designed to work across walking speeds for a typical wearer weighing 250 lbs. Other design input parameters include motor diameter and winding characteristics; series elasticity stiffness; ball-screw transmission ratio; battery and power supply topology and switching frequency. The result is a multi-variable design output space that includes walking range; acoustic energy (torque ripple harmonics) in the 1.5 kHz-3 kHz audio band; design life and prosthesis weight.

A robust design is suitable for a broad range of wearer weights, including from approximately 185 lbs. to approximately 250 lbs., as may be common amongst soldiers expected to use the device 600. However, the device 600 is usable by wearers outside of this range. The battery may be capable of powering at least 2000 steps for a 185 lb. wearer. The device 600 may be designed to output a peak torque from the muscle tendon units 602, 604 of at least approximately 150 N-m, and may output a peak power of at least approximately 800 watts. The ankle 602 may have a range of rotation of at least approximately 25° and the knee 604 may have a range of rotation of at least 130°.

The devices 200, 400, 600 described above may rely on processing of the IMU state to detect gait cycle state transitions and to determine intra-step estimates of walking speed, allowing for intrinsic control of reflex strength in accordance with walking speed. Further, intrinsic measures of torque can detect the difference between heel-strike first and toe-strike first gait cycles, sufficient to nuance the control for stair ascent (toe-strike first) in relation to normal walking on sloping ground (heel-strike first). Separate or complementary controls may be used to control biomimetic leg systems (ankle-foot and/or knee) for stair ascent/descent and steep sloping terrain modalities. In full leg systems, the knee prosthesis may be controlled to define the trajectory of the ankle-foot in multi-terrain environments. IMU-based kinematic reconstruction algorithms may use the IMU to determine the six degree-of-freedom (6 DOF) inertial state; the homogeneous transformation that defines the orientation and origin of a coordinate system with respect to ground of the lower extremity link that connects the ankle and knee joint. Self-calibrating algorithms, which may be considered a "zero-velocity update" (ZVUP) that occurs at a "zero moment point" (ZMP), can compute the inertial state within a gait cycle without a priori information averaged from prior steps. By combining the inertial state with ankle and knee joint encoder feedback and knowledge of wearer shoe size and the kinematic transforms between ankle, knee and hip, the trajectory of the toe, heel, ankle, knee and hip can be computed in real-time.

Figure 7A:
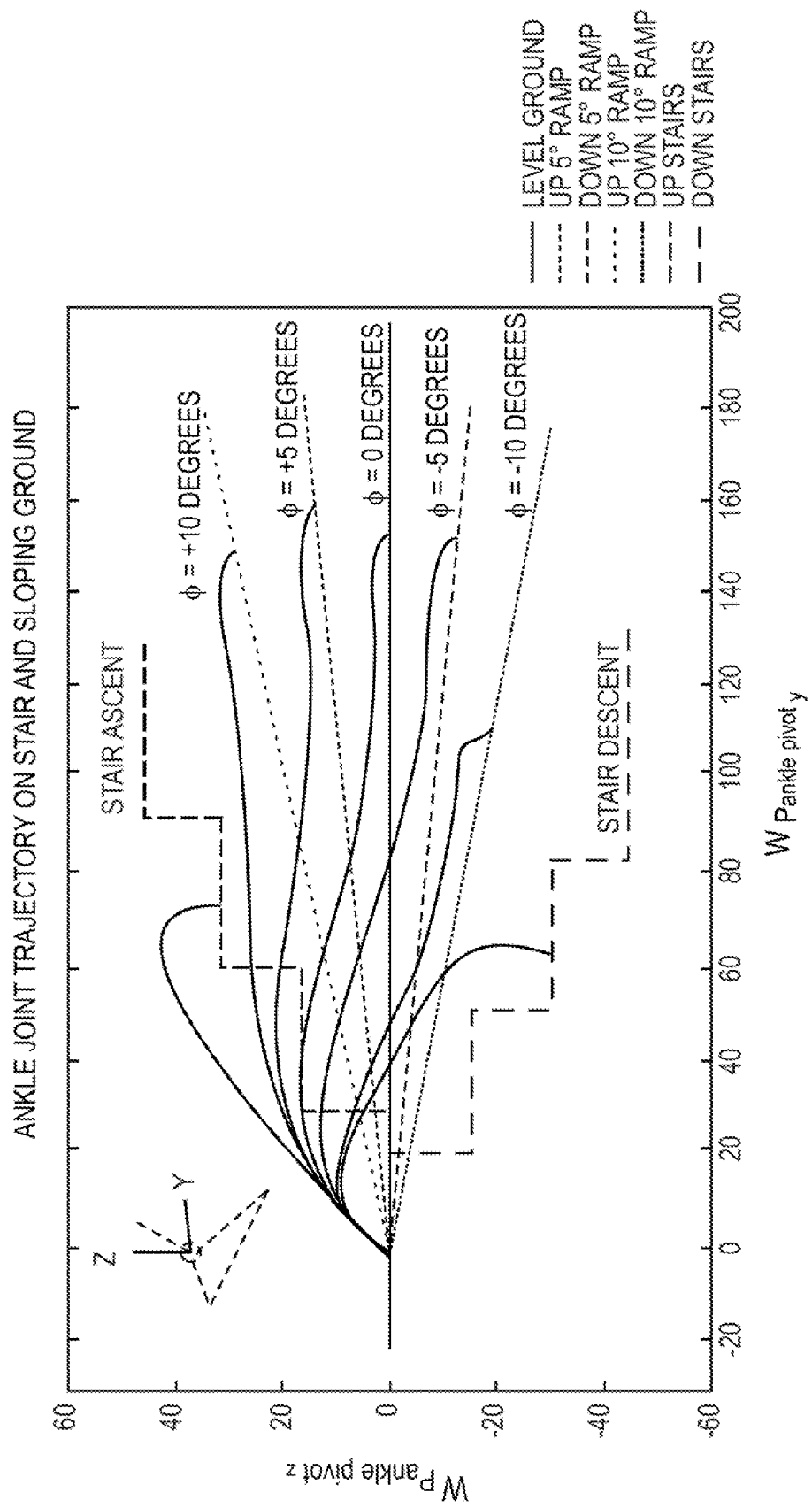
FIGS. 7A and 7B are graphs of joint trajectories for an ankle and knee, respectively, in various modalities.
Figure 7B:
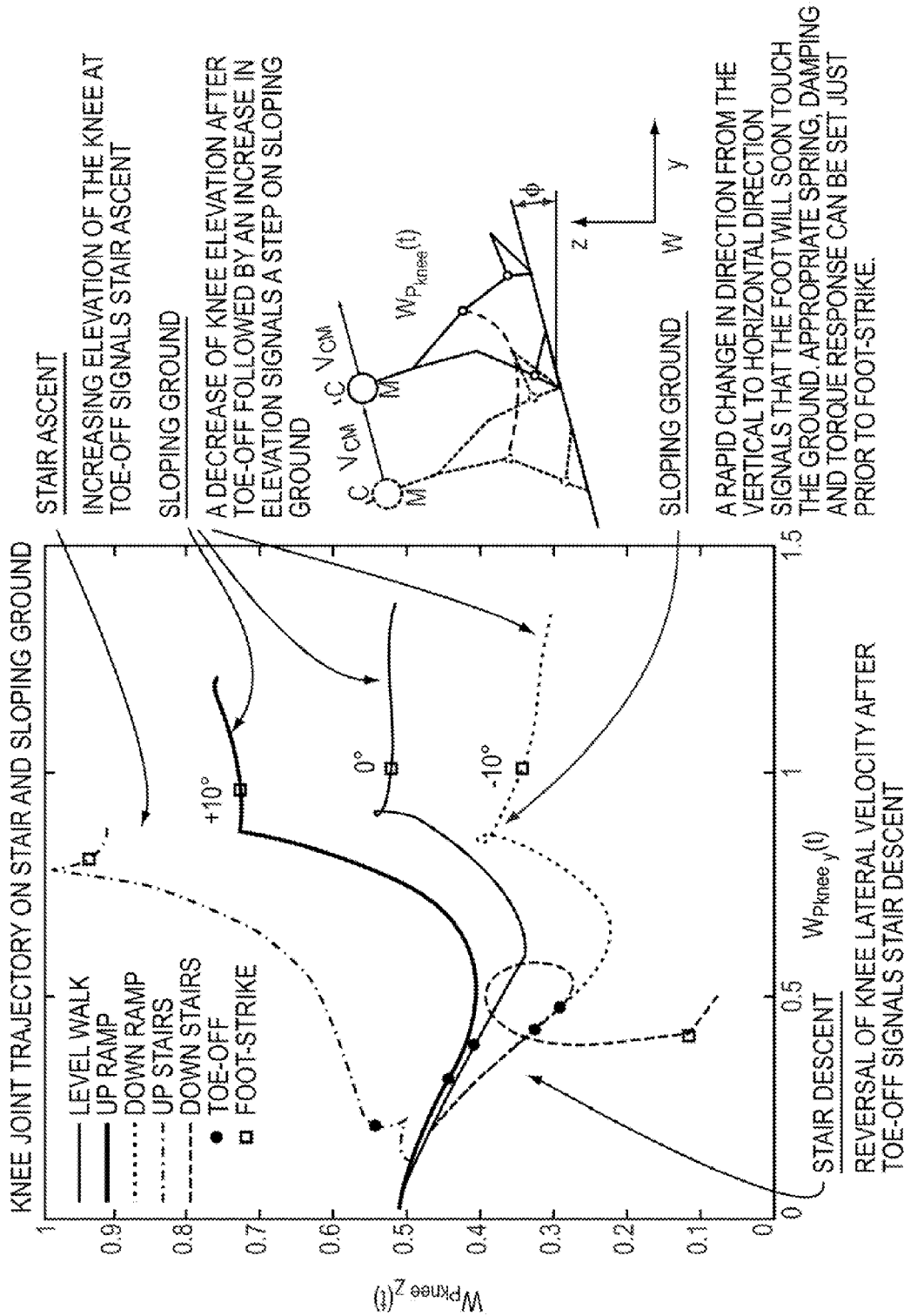

FIG. 7A illustrates offline-kinematic reconstructions of ankle and knee trajectory using the IMU and intrinsic sensing from the ankle device, superimposed on stair and sloping ground terrain modalities. In this manner, high-quality inertial state information can be used to discriminate between different terrain modalities in real-time. As shown in FIG. 7B, irregular knee paths may be used to anticipate foot-strike in a wide range of terrain modalities. As shown, the folding back of knee path is a precursor to foot strike. Knowing when foot-strike is reached, ankle-foot trajectory can be used to sense the stair parameters or terrain slope and the "momentum" of the impending strike, from which appropriate pre-strike joint mechanical impedance, equilibrium and reflex characteristics can be nuanced.

Trial data from the walking tests may be treated as known "test vector" inputs to the kinematic reconstruction and pattern recognition algorithms. Terrain modality discrimination to disambiguate between level ground, sloped and stair terrain modalities, both in the swing phase and the stance phase, may also be tested and validated statistically. Other reference biomechanical inputs in addition to those described above may be used to design ankle and knee reflex response characteristics. Preferred muscle models may be identified using goodness of fit and efficiency as a function of terrain slope and walking speed (e.g., for slopes of +10, +5, 0, −5, and −10 degrees for walking speeds of 0.75, 1.0, 1.25, 1.5 and 1.75 m/s). Similar techniques may be used in defining the neuromuscular model as a function of polarity (stair ascent vs. descent), stair characteristics, and stair ascent/descent rates.

A functional test stand may be used as a bench platform for life-testing actuators and for engineering/manufacturing calibration of SEA torque-displacement models. The test stand may employ a backdrive mechanism mounted on a precision, 6DOF, force/torque sensor to apply torque or position input/stimulus to the prosthesis joint under test. While the ankle test configuration is described for reference purposes, similar configurations may be used for other components. One configuration may be used to verify the MTU and neuromuscular control response characteristics, including, but not limited to, joint (or motor) torque, displacement/velocity, work impedance, power, design-life and battery energy per cycle. In the tests of biomechanical capability, the backdrive mechanism will "play back" a joint displacement trajectory, $\theta(t)$, that emulates the trajectory in an intact ankle. The MTU under test may deliver a joint torque, $\Gamma(t)$, or motor torque, $\tau(t)$, as appropriate in synchrony with the displacement trajectory. This way, a repetitive test can be applied corresponding to theoretical or actual gait cycles to validate MTU/Neuromuscular performance. Some testing embodiments may include an in-line, robotic calibration and verification of the IMU using a robotic work cell. For example, a Staubli (Pfäffikon, Switzerland) RX90 robot may be used to supply a calibrated motion input from which the calibration and validation can be accomplished. The kinematic reconstruction verification may use this method to verify trajectory computations, including ZVUP.

Certain kinematic reconstruction validation may be accomplished by comparing results, off-line, in relation to the joint trajectories computed using stereo photogrammetric methods. Raw IMU data may be recorded simultaneously with the stereo photogrammetric acquisition during biomechanical testing. On an off-line basis, the kinematic reconstruction results may be validated with the stereo photogrammetric (gold standard) used as the reference. Terrain discrimination algorithms to be deployed may also be tested against this reference data.

The MTU joint torque and displacement may be calibrated individually on the functional test stand, using an adaptor built for holding the prosthesis to permit this isolated testing and calibration. Once calibrated, the torque-displacement predictions may be compared to the backdrive stimulus reference using special stimulus trajectories designed for the purpose, thereby accomplishing sensing, calibration and algorithmic verification of the MTU torque/displacement models.

In a manner consistent with the kinematic reconstruction validation above, MTU torque and displacement may be recorded during clinical evaluation. The biomechanical computations arising from the joint torque-displacement predictions from the stereo photogrammetric and force plate data can be used as a reference with which to validate the MTU torque-displacement predictions on an off-line basis. Once validated, in situ measurements of torque-displacement and mechanical work can be used to validate the tuning of the neuromuscular-derived MTU control parameter vectors and to compare, in the form of a dashboard, the measurements to predefined reference measures of joint displacement, work and power across walking speeds derived from an inverse dynamics calculation on human kinetic and kinematic walking data. Once validated, in situ measures of electro-mechanical efficiency may be collected in real-time, gait-cycle-by-gait-cycle.

Sound level comparisons between the radial-flux-based and the transverse-flux-based prostheses can be made in an area with an ambient noise level of <40 dB. A microphone (MIC) can be placed in a number of locations relative to the test object including:

Close Proximity: MIC attached to ankle via mounting bracket such that separation distance<6".

Prosthesis Wearer Perception: MIC attached to user's head/upper-torso to accurately capture perception of user.

Observer Perception: MIC placed in fixed location at a 1 m distance from the wearer to accurately capture perception of observer. This step may be used to account for system specific sound projection characteristics and the frequency dependent nature of sound propagation.

Preprocessing can include application of an A-frequency-weighting filter to the raw sound level measurements (per IEC 61672). The acoustic comparison may be made within the 1.5-3 kHz frequency range according to the mean/maximum sound pressure level for each step event and an equivalent continuous sound level.

The biomimetic transfemoral system 600 may also be tested in its ability to reduce the metabolic economy to walk compared to an intact limb population. The metabolic rate may be calculated from measures of oxygen consumption and carbon dioxide production while amputees and age, weight and height-matched non-amputees walk on level ground and sloped ($\pm 10$ degrees) surfaces. Measures of oxygen uptake and carbon dioxide production may be obtained using a portable, lightweight, breath-by-breath telemetric system (e.g., the Cosmed K4b2 (Rome, Italy)). Study participants walk around an indoor track next to an electric vehicle programmed to move at their self-selected speed when using the biomimetic prosthesis, collecting data for a minimum of 8 minutes. The final three-minute section of the recordings may be selected after steady-state conditions have been reached. The metabolic and walking speed data confirm when a transfemoral prosthesis is capable of biological ankle and knee mechanics to normalize metabolic economy and self-selected walking speed during level-ground and sloped ($\pm 10$ degrees) ground surface ambulation.

To assist in measuring human and prosthetic knee and ankle mechanics, reflective markers may be positioned on the body and data may be recorded using a stereo-photogrammetric system. At each gait speed, researchers measure whole body kinematics and kinetics from the right and left sides of the body, e.g., during ten trials per subject and condition. Reflective markers may be applied to the skin, including on the following bony landmarks: bilateral anterior superior iliac spines, posterior superior iliac spines, lateral femoral condyles, lateral malleoli, forefeet and heels. Additional markers may be rigidly attached to wands over the mid-femur and mid-shaft of the tibia. For transfemoral amputees, the tibia, lateral malleoli, forefeet and heel markers may be placed on the prosthesis at appropriate locations matching the intact limb. 3D pelvic and bilateral lower extremity joint kinematics may be collected by means of an eight-camera motion analysis system, sampling at 120 frames per second. 3D whole body kinetics may be collected by means of force plates (AMTI) sampling at 1080 Hz. The following anthropometric measures may be collected, along with motion analysis and force platform measures, to calculate joint kinematics and kinetics: body weight, height, leg length (measured from medial malleolus to anterior superior iliac spine), knee width, and ankle width.

Joint torque and power calculations may be based on the mass and inertial characteristics of each lower-extremity segment, the derived linear and angular velocities and accelerations of each lower extremity segment, and ground reaction force and joint center position estimates. For each trial, bilateral hip, knee, and ankle joint kinematic and kinetic data during walking may be derived. Position data recorded using the motion capture system may be computed in three planes (sagittal, coronal, and transverse) using standard software provided with the system. Ground reaction forces may be measured synchronously with the kinematic data using two embedded force platforms (AMTI). Joint kinetics in each plane may be calculated using a full-inverse dynamics model. For the transfemoral ambulation trials, the human model can be modified to accurately represent the mass distribution of the prosthesis. To evaluate the accuracy of the full-inverse dynamics model, the intrinsic sensory measurements of prosthetic knee and ankle torque and power will be compared to the torque and power calculated from the inverse dynamics model. At each gait speed and test participant, average curves for each subject's knee and ankle position, velocity, torque and power may be obtained from the collected trials. Human knee and ankle mechanics from the individuals with intact limbs may then be compared to prosthetic knee and ankle mechanics at equivalent gait speeds.

Figure 8:
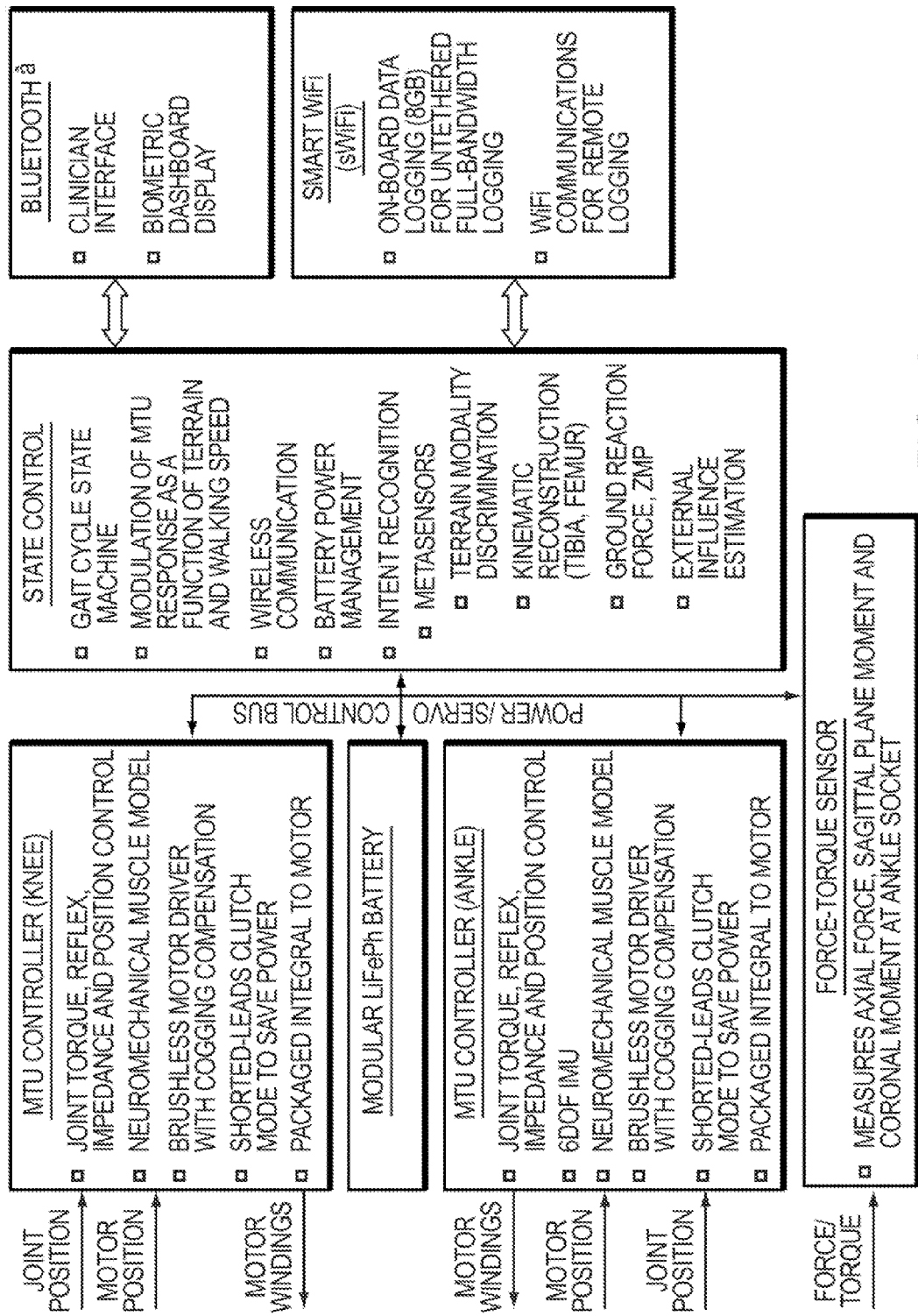
FIG. 8 is a block diagram of a control system for a leg device, in accordance with one embodiment of the invention.

The use of neuromuscular-inspired MTU control software may emulate the biological response of an intact limb, thereby normalizing metabolic walking economy and biomechanical response, as depicted in FIG. 8. The implicit control architecture may be complementary or separate from the control architecture previously described, including the use of non-linear positive force feedback to achieve a reflex behavior. To create the more complex reflex dynamics in a multi-axis leg prosthesis, the control structure may be more generalized and aligned to real muscle activation models. A metasensor that measures the ground reaction force and ZMP may be created by combining the force-torque and the IMU-based kinematic reconstruction.

Intrinsic inertial sensing, signal processing and pattern recognition may be used to achieve intra-step terrain adaptation—thereby enabling seamless terrain modality transitions. The kinematic reconstruction described above may be applied to the multi-dimensional leg system 600. Pattern recognition of both ankle and knee trajectories may be used to discriminate between steep slope and stair ambulation.

Closed-loop torque control algorithms may be designed using the calibrated, SEA, torque-displacement models as the primary feedback. The first SEA resonant frequency may fall in the range of 45-50 Hz, enabling a feed forward-enabled closed loop bandwidth of 25 Hz—sufficient to make the MTU response substantially invariant with transmission friction variation. Other feedback systems are described in detail below. Motor torque cogging compensation firmware can also be designed. Various neuromuscular models may be embedded in the MTU to test torque-reflex and impedance response characteristics across walking speeds (e.g., at 0.75, 1.0, 1.25, 1.5, and 1.75 m/s).

Figure 9:
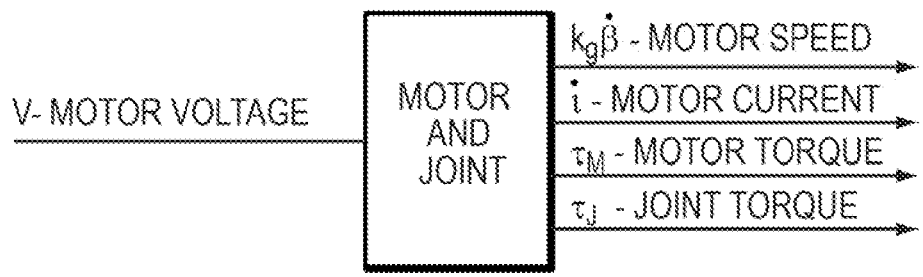
FIG. 9 is a block diagram of signals associated with a motor and joint system, in accordance with one embodiment of the invention.

Known prosthetic and/or orthotic devices typically employ a current-feedback system to control the operation of the motor in an SEA. Generally, in such a system voltage applied to the motor is manipulated so as to produce a desired result, e.g., to deliver the required motor torque. In order to guide the voltage manipulation the known systems only use the motor current in a feedback control system. FIG. 9, however, depicts other signals in addition to motor voltage and current that may also be associated with a feedback system for the device. These signals include motor torque, joint torque, and motor speed. In various embodiments described below one or more of these other signals are used instead of or in addition to motor current to control the motor voltage so to produce a desired torque characteristic, e.g., a joint torque, impedance, and/or equilibrium. Various combinations of the signals may or may not be available for measurement over a period of time. High fidelity joint torque control may be difficult in SEAs, particularly those where the series-elastic element is used as a catapult to amplify motor power at the joint. In these SEAs, the spring stiffness is relatively low (e.g., 350 Nm/rad in an ankle joint). In such a case, the first SEA resonance, which arises from the E reflected motor inertia reacting with the series-spring, can be as low as 8 Hz. In conventional joint torque controllers, the bandwidth may be limited to a frequency less than this first resonance, resulting in an often underdamped response that cannot emulate biological muscle-tendon units.

Figure 10:
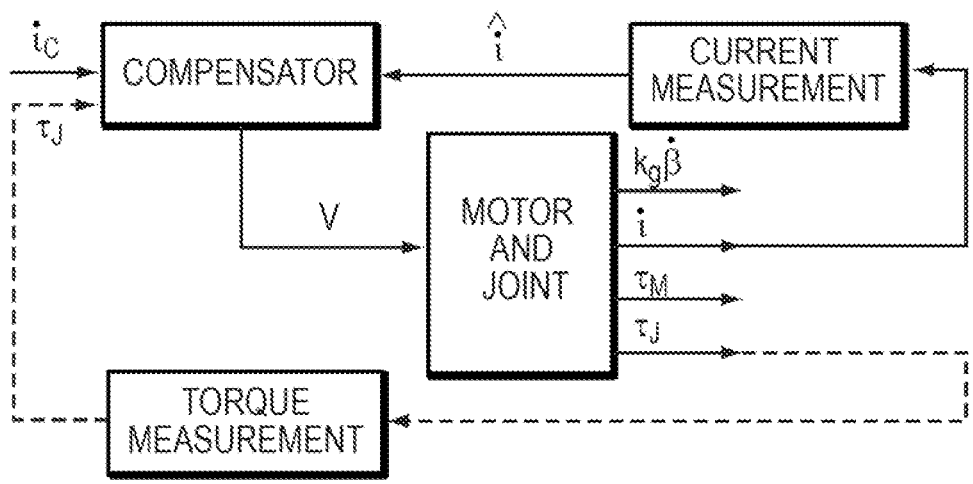
FIG. 10 is a block diagram of a current feedback loop, in accordance with one embodiment of the invention.

FIG. 10 depicts one such system that controls motor current as a surrogate for joint torque, creating a command current signal, and applying feedback compensation that drives motor voltage so as to make the motor torque track the command. In this open-loop joint torque control, motor cogging, motor ripple, SEA transmission friction, backlash, and other non-linear dynamics will influence the degree to which the joint torque can track the commanded value. An outer joint torque compensator may be applied to address this issue. One known system uses joint torque in addition to motor current to compute motor voltage. However, the manipulation of the command current signal in such a system often makes the control system very hard to control or even unstable as shown in the sequel, due to resonance characteristic of the associated physical device, allowing only a limited joint torque bandwidth for controller operation in this configuration. These problems often exist when the inner current loop is closed and joint torque error due to the SEA resonance dynamics is not eliminated by the addition of an outer joint torque loop. As described with reference to FIG. 12, the instability and/or bandwidth control problems may be overcome by measuring motor speed and using this variable in an EMF feedforward compensator.

Figure 11:
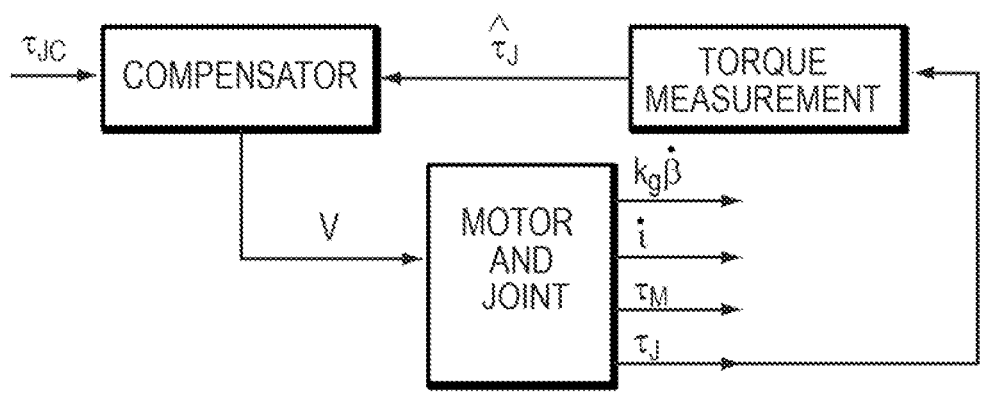
FIG. 11 is a block diagram of a system for directly controlling joint torque, in accordance with one embodiment of the invention.

FIG. 11 depicts a system where joint torque is measured and the corresponding signal used instead of the measured current to compute a voltage that produces desired results. In addition to fewer limitations on the bandwidth of the compensator, this configuration more easily enables the joint torque to follow a joint torque command signal that produces desired results, in contrast with the current command signal described above. The joint torque is the most naturally commanded signal, while a current signal tends only to be related to usual performance objective through complicated interactions with other variables.

Figure 12:
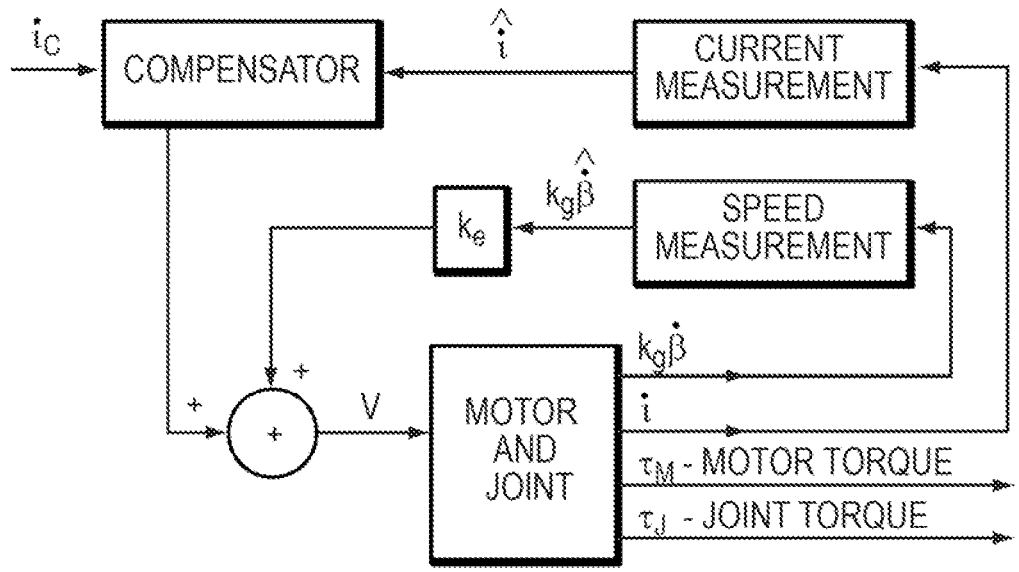
FIG. 12 is a block diagram of an emf feedforward with current feedback loop, in accordance with one embodiment of the invention.
Figure 13:
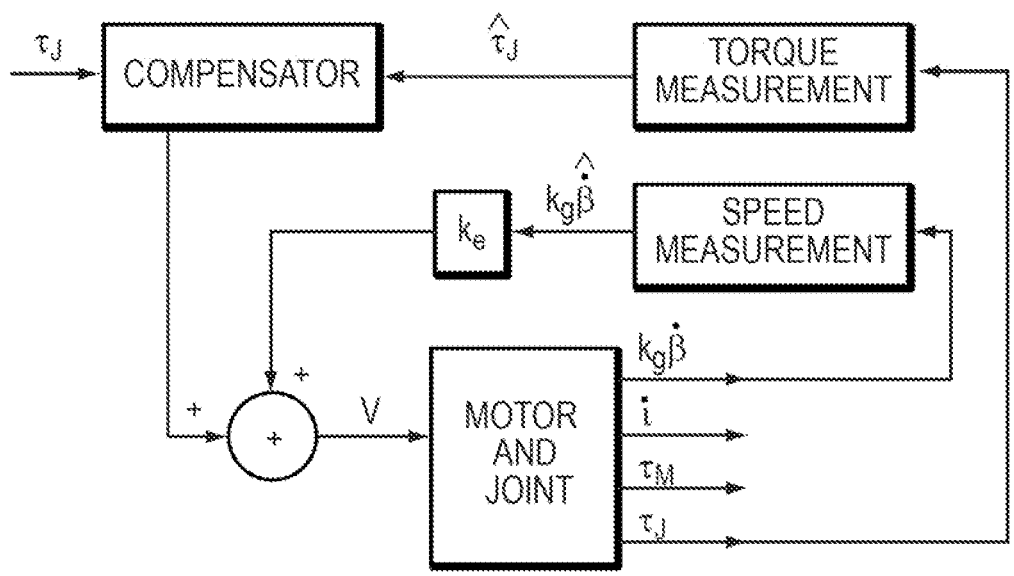
FIG. 13 is a block diagram of an emf feedforward with joint torque feedback loop, in accordance with one embodiment of the invention.

FIGS. 12 and 13 illustrate configurations where voltage is computed using two components: a component that is a scaled measurement of a measurement of the motor speed and a feedback component. Feeding back a scaled measurement of the motor speed is called EMF feedforward, as the signal can provide an estimate of the electromotive force produced within the motor while canceling the effect of this force. Measuring motor speed is one way of producing this estimate of the EMF, though other methods for producing the estimate that are known to those of skill in the art are considered within the scope of this disclosure. These other methods could include the use of Kalman-filter based observer to estimate the EMF from motor winding voltage and phase current.

When using the EMF estimate, the resulting system may become easier to control, such as by enabling the use of other signals in conjunction with the EMF estimate to produce desired results. FIG. 12 depicts a current feedback loop in conjunction with the EMF feedforward. The EMF feedforward allows an improved performance in the current feedback loop. FIG. 13 depicts a joint torque feedback loop as in conjunction with the EMF feedforward. The use of other feedback in conjunction with the EMF feedforward, or using the EMF feedforward alone, is also contemplated.

A representative dynamic model of a typical SEA that illustrates the challenges inherent in designing a controller that achieves a torque loop bandwidth not limited by the first resonance is described below. To model a foot and spring, a motor may be attached to an imaginary member which represents the foot position if the spring were in neutral. Thus the angle β associated with this member is the motor angle divided by the gearing constant. $k_g$, with $k_g$ in one embodiment being approximately 220.

Variable and Coefficient List:
θ Angle of the foot (rad)
β Angle of the imaginary member associated with neutral spring (rad)
$k_g$β Angle of the motor shaft (rad)
$k_g$ Gearing multiplier (approx. 220)
$L_f$ Length of foot from ankle (0.28 meters)
$J_f$ Moment of inertia of foot In an embodiment, the foot may be assumed to weigh 1.5 lbs, which acts as a point mass halfway down the foot. A force of 1.5 lbs corresponds to 6.67 Newtons or kg*m/(sec.$^2$. Dividing by acceleration of gravity 9.8 m/(sec)$^2$ gives a mass of 0.68 kg, resulting in a value of $J_f$ of 0.68*(0.14)$^2$=0.013 kg*m$^2$ (0.14 is $L_f$/2).

$J_M$ Moment of inertia of the motor shaft
$K_S$ The spring constant.

When β>θ the spring is stretched and pulling with $K_S$=350 N*m/rad, and when β<θ the spring is compressed and pushing with $K_S$=1200 N*m/rad.

$\tau_E$ External torque on the foot. If a person of weight W steps onto the toe of the foot, $\tau_E$=−W*$L_f$. The negative sign indicates the torques work to decrease θ. A person weighing 225 lbs weighs 1000 Newtons. With a foot measuring 0.28 m, the torque applied would be 280 N*m.

$B_f$ The damping in the ankle joint. Due to friction, it creates a force opposing the angular velocity of the foot.
$B_M$ The damping in the motor due to friction.

The basic kinematic equation $\tau = J*\ddot{\theta}$ applied to the foot around the ankle joint gives:

$$\tau_E + K_S(\beta-\theta) - B_f\dot{\theta} = J_f\ddot{\theta} \tag{1}$$

The basic kinematic equation $\tau = J*\ddot{\theta}$ is now applied to the motor shaft, representing the motor angle as $k_g*\beta$.

$$\tau_M - \frac{K_S}{k_g}(\beta-\theta) - B_M k_g\dot{\beta} = J_M k_g\ddot{\beta} \tag{2}$$

The system may be changed to average angle and difference. New variables may be defined as follows:
$\phi_A = 0.5(\beta+\theta)$; the average position between the foot and the imaginary member
$\phi_D = 0.5(\beta-\theta)$; the difference position between the foot and the imaginary member $$J = J_f + (k_g)^2 J_M; B = B + (k_g)^2 B_M;$$

The two equations become:

$$\tau_E + k_g\tau_M - B\dot{\phi}_A + (B_f - B_M k_g^2)\dot{\phi}_D = J\ddot{\phi}_A + (J_f - (k_g)^2 J_D)\ddot{\phi}_D \tag{3}$$

$$-\tau_E + k_g\tau_M - 2K_S\phi_D - B\dot{\phi}_D + (B_f - B_M k_g^2)\dot{\phi}_A = J\ddot{\phi}_D + (J_f - (k_g)^2 J_D)\phi_A \tag{4}$$

When the effects of the differential damping terms are considered to be negligible, the general structural elements can be seen. The dynamics of the mechanical system may be modeled as:

$$\tau_E + k_g\tau_M - B\dot{\phi}_A = J\ddot{\phi}_A \tag{5}$$

$$-\tau_E + k_g\tau_M - 2K_S\phi_D - B\dot{\phi}_D = J\ddot{\phi}_D \tag{6}$$

The equations for the motor dynamics are:

$$L\frac{di}{dt} + Ri = V - K_e k_g\dot{\beta} \tag{7}$$

$$\tau_M = T_M i \tag{8}$$

Taking transforms:
$$Lsi + Ri = V - K_e k_g s\beta \tag{9}$$

$$\tau_M = T_M i \tag{10}$$

The back emf of the motor is represented by the term $K_e k_g s\beta$ $$\tau_E + k_g\tau_M - Bs\phi_A = Js^2\phi_A \tag{11}$$

$$-\tau_E + k_g\tau_M - 2K_S\phi_D - Bs\phi_D = Js^2\phi_D \tag{12}$$

The SEA drives the joint through a spring that serves as a catapult to amplify motor power at the joint. This form of bionic muscle-tendon unit may serve as the basis for emulation of the biomechanical response of an intact limb.

Figure 14:
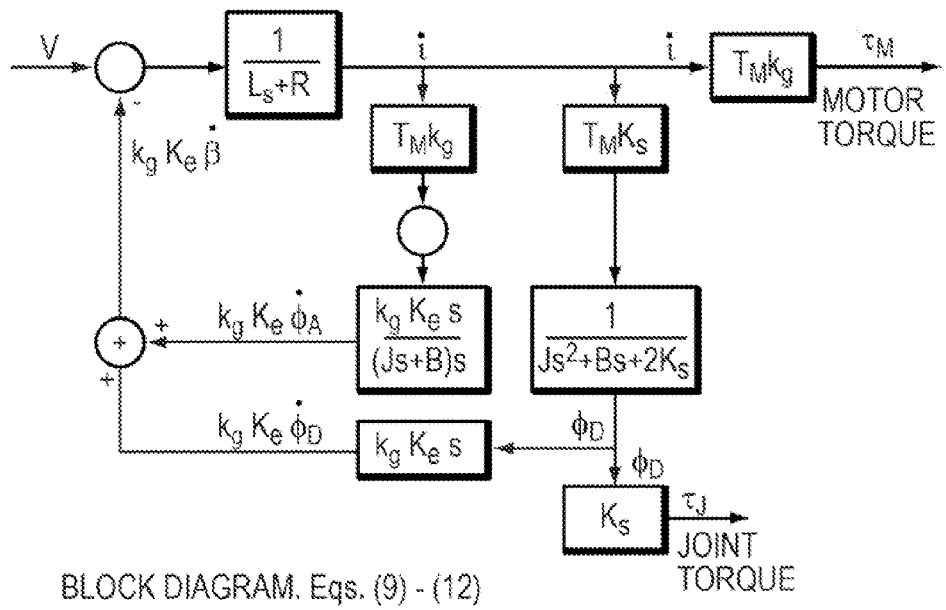
FIG. 14 is a block diagram of a model for using motor current to compute a feedback signal to manipulate voltage to control motor torque, in accordance with one embodiment of the invention.
Figure 15:
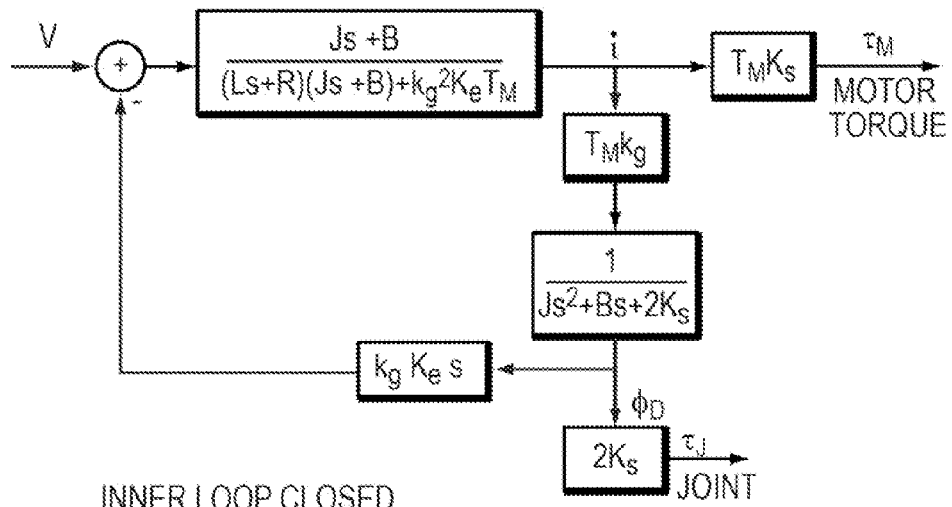
FIG. 15 is a block diagram of a model for using motor current to compute a feedback signal to manipulate voltage to control motor torque without an inner current-feedback loop, in accordance with one embodiment of the invention.

FIG. 14 is a block diagram of the system, as closely approximated by the equations (9)-(12). FIG. 15 depicts a system that achieves a similar result, i.e., the required joint torque characteristic, but the inner current-feedback loop is eliminated.

The open-loop joint torque system depicted in FIG. 14 relies on use of the motor current to compute a voltage to be applied to the motor windings to control joint torque. The controlled motor torque must in itself account for the effects of the complicated transfer function between the motor torque and the joint torque. Also, the complex loop involving the back emf proportional to β is not treated directly but its effects are assumed to be negated by the disturbance rejection properties of feedback.

Figure 18:
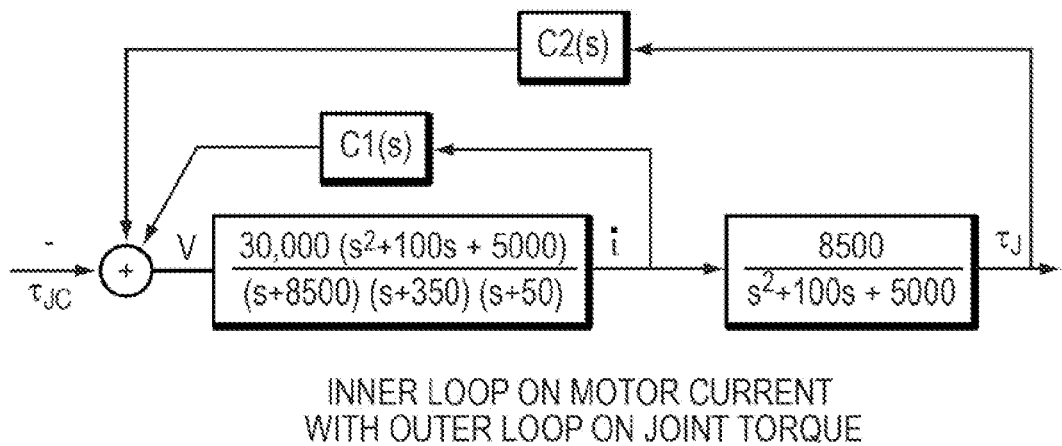
FIG. 18 is a block diagram of a model for using a measurement of joint torque through two compensators to compute a voltage signal, in accordance with one embodiment of the invention.

However, there are significant limitations of using current feedback in this setting. From the partially reduced system of FIG. 15, it can be seen that the poorly damped spring dynamics appear as poles in the return transfer function in the naturally occurring back emf feedback within the model. This means that, when the current loop is closed, as shown in FIG. 14, the effects of the spring element appear as a pair of zeros near the imaginary axis in the transfer function between the voltage and the motor current. When a current-loop controller with these dynamic limitations is embedded in a closed-loop torque control, as shown in FIG. 18, the closed loop torque response either exhibits a bandwidth far below the resonance or exhibits an underdamped response, neither of which is useful in emulation of biological muscle tendon unit response.

Using a direct measurement of joint torque, a wider bandwidth and more robust closed-loop control system is possible. Here, proportional-integral compensation applied to the joint torque tracking error will generate a stable response that extends beyond the first resonance. In the system depicted in FIG. 15, the resonant spring dynamics appear in the forward path of the joint torque controller rather than the feedback path. Therefore, these dynamics do not appear as troublesome zeros in a loop that measures the joint torque and manipulates that signal to produce a compensating voltage input. In general, poorly damped zeros in a feedback control design limit the bandwidth and effectiveness of the control loop, as described above. Indeed, since the poorly damped poles are substantially eliminated) i.e., legitimately cancelled by the zeros arising from the same dynamics in the naturally occurring back emf loop), the transfer function between the motor's voltage and the joint torque is quite benign (without oscillatory dynamics) and amenable to a PI or PID controller.

Figure 16:
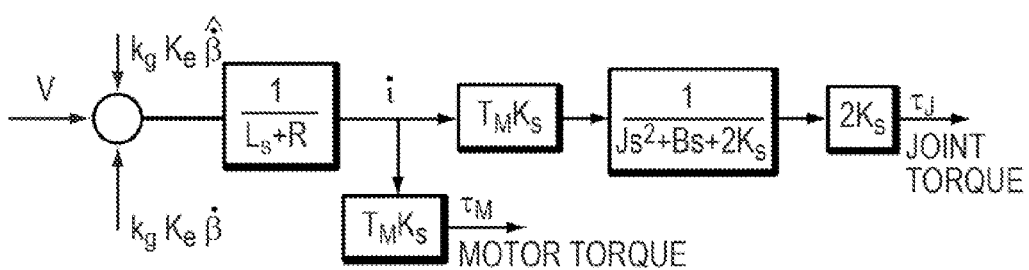
FIG. 16 is a block diagram of a model with emf feedforward, in accordance with one embodiment of the invention.

FIG. 16 depicts a further improved system with the inclusion of emf feedforward in a closed-loop torque controller with embedded current loop. Here the feedforward substantially eliminates the underdamped dynamics, enabling simple compensation in the outer torque loop. A measurement or derived estimate of the motor speed $\dot{\beta}$ is used in a controller to cancel the effect of the back emf. As shown in FIG. 16, this greatly simplifies the dynamics of the system. A feedback controller measuring and feeding back either the current i or the joint torque can be used in addition to the emf feedforward to reduce sensitivity to any remnant error in the estimation of the motor speed and other modeling errors. A simple PI loop using the motor current can control the motor torque while a PI or PID loop using the joint torque may produce excellent control of the joint torque.

Figure 17:
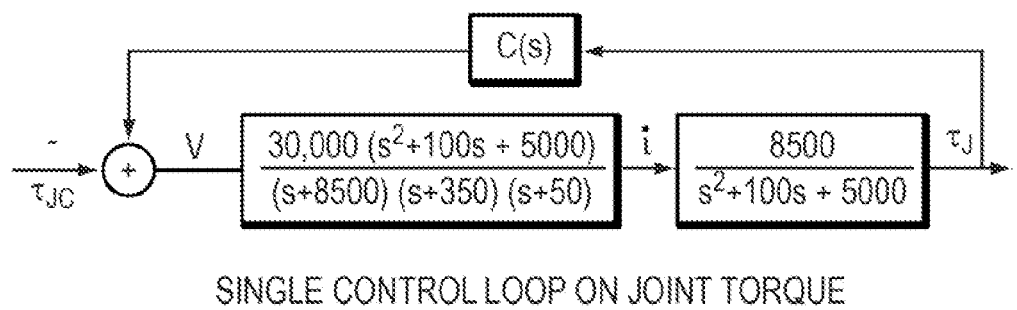
FIG. 17 is a block diagram of a model for using a measurement of joint torque through a single compensator to compute a voltage signal, in accordance with one embodiment of the invention.

FIG. 17 is a block diagram of a model using a measurement of joint torque through a single compensator to compute a voltage signal that produces a desired result. The blocks of FIG. 17 have been filled with typical transfer functions for a typical joint problem; one block giving a transfer function from motor voltage v to motor current i and a second block giving a transfer function from motor current i to joint torque $\tau_J$. For the single loop, only the product of the two blocks may be considered so that the poorly damped poll pair that originates with the spring is exactly cancelled by the zero pair in the first block that originates in the same physical element. The resulting dynamics allow for the design and implementation of a compensator C(s) to follow the command signal $\tau_{JC}$. C(s) may be a PI controller.

By contrast, a model of the known motor controllers, described with reference to FIG. 18, includes two compensators arranged in an inner loop using the motor current i and an outer loop using the joint torque $\tau_J$. The inner loop may have to contend with a poorly damped zero pair in the first block, though two systems may be expected to perform similarly by setting:

$$C2(s) = C(s) - \frac{s^2 + 100s + 5000}{8500} C1(s) \quad (13)$$

Thus, the C2 compensator needed to make the systems perform the same may be more complex than systems requiring only a single compensator, in addition to the complexity of making multiple measurements and implementing multiple compensators.

It should be understood that for those skilled in the art, the control architecture described here can be extended to bionic ankles that employ physical or SEA-applied virtual, unidirectional parallel elastic elements where the torque-displacement characteristics of these can be calibrated before use. Further, while the control architecture has been applied to leg prostheses, the principles can be readily extended to orthotic, exoskeletal or humanoid applications in lower-extremity augmentation of ankles, knees and hips.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The compositions, components, and functions can be combined in various combinations and permutations, to achieve a desired result. For example, all materials for components (including materials not necessarily previously described) that are suitable for the application are considered within the scope of the invention. Accordingly, the described embodiments are to be considered in all respects as only illustrative and not restrictive. Furthermore, the configurations described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A method for controlling a motorized, artificial limb having an actuator, the actuator comprising a motor coupled in series with an elastic element, to apply a torque characteristic to a joint, the method comprising the steps of:
   applying a voltage to windings of the motor;
   measuring the torque characteristic at the joint;
   computing, using a hardware controller, a torque characteristic error as a difference between a target torque characteristic and the measured torque characteristic, the computing comprising applying a model in which a back electromotive force (EMF) of the motor occurs; and
   controlling, using the hardware controller, the applied voltage independently of motor current, to reduce the torque characteristic error, the controlling comprising estimating a speed of the motor, and using the estimated speed of the motor to cancel the back EMF in the model.

2. The method of claim 1, wherein the torque characteristic comprises at least one of a joint torque, a joint impedance, and a joint equilibrium.

3. The method of claim 1, wherein the applied voltage is controlled solely based on the target torque characteristic and the torque-characteristic error.

4. The method of claim 1, wherein the controlling step avoids at least one of: (i) computation of motor current and (ii) computation of an adjustment to the motor current supplied to the motor to achieve the target torque characteristic.

5. The method of claim 4, wherein the controlling step avoids measurement of motor current and using, at least in part, the measured current for adjusting the motor current.

6. The method of claim 1, wherein the limb control method is independent of a resonance frequency associated with the coupling of the motor and the elastic element.

7. The method of claim 1, wherein the step of measuring the torque characteristic at the joint comprises measuring at least one of an angular position of the motor and an angular position of the joint.

8. The method of claim 1 further comprising:
   estimating voltage corresponding to the back electromotive force related to the motor speed; and
   controlling the applied voltage based on, at least in part, the estimated voltage corresponding to the back electromotive force.

9. The method of claim 1, wherein the artificial limb comprises at least one of a prosthetic limb and an orthotic limb.

10. The method of claim 1, wherein the joint is at least one of an ankle joint and a knee joint.

11. An artificial limb system comprising:
- an actuator coupled to a joint for applying a torque characteristic thereto, the actuator having a motor coupled in series with an elastic element;
- a power source for applying a voltage to windings of the motor;
- at least one sensor for estimating the torque characteristic at the joint; and
- a hardware controller configured to: (i) compute a torque characteristic error as a difference between a target torque characteristic and the torque characteristic measured by the sensor the computing comprising applying a model in which a back electromotive force (EMF) of the motor occurs, and (ii) control the applied voltage independently of motor current, to reduce the torque characteristic error, the controlling comprising estimating a speed of the motor, and using the estimated speed of the motor to cancel the back EMF in the model.

12. The system of claim 11, wherein the torque characteristic comprises at least one of a joint torque, a joint impedance, and a joint equilibrium.

13. The system of claim 11, wherein the controller is adapted for controlling the applied voltage solely based on the target torque characteristic and the torque-characteristic error.

14. The system of claim 11, wherein the controller is adapted for controlling the applied voltage without using a computation of at least one of: (i) motor current and (ii) an adjustment to the motor current supplied to the motor to achieve the target torque characteristic.

15. The system of claim 14, wherein the controller is adapted to avoid at least partially using a measurement of motor current for an adjustment thereof.

16. The system of claim 11, wherein the controller is adapted such that a controller response is independent of a resonance frequency associated with the coupling of the motor and the elastic element.

17. The system of claim 11, wherein the artificial limb system comprises at least one of a prosthetic limb system and an orthotic limb system.

18. The system of claim 11, wherein the joint is at least one of an ankle joint and a knee joint.

19. The system of claim 11, wherein the sensor is selected from the group consisting of a joint encoder, a torque sensor, a deflection sensor disposed on the series elastic element, a joint angle sensor, and a motor angle sensor.

20. The system of claim 11 further comprising a motor encoder for measuring the motor speed, wherein the controller is further adapted to: (i) estimate voltage corresponding to the back electromotive force related to the motor speed, and (ii) control the applied voltage based on, at least in part, the estimated voltage corresponding to the back electromotive force.

21. The system of claim 11 further comprising an observer to estimate voltage corresponding to back electromotive force, and the controller is adapted to control the applied voltage based on, at least in part, the estimated voltage corresponding to the back electromotive force.

22. The system of claim 11 further comprising a linkage having a plurality of links, wherein:
- the linkage is coupled to the joint; and
- the motor is coupled to a first link in the linkage and the elastic element is coupled to a second link in the linkage.

* * * * *